United States Patent
Young et al.

(10) Patent No.: US 8,604,447 B2
(45) Date of Patent: Dec. 10, 2013

(54) SOLAR METROLOGY METHODS AND APPARATUS

(75) Inventors: Scott Young, Soquel, CA (US);
Guoheng Zhao, Palo Alto, CA (US);
Ady Levy, Sunnyvale, CA (US); Marco Guevremont, San Francisco, CA (US);
Neeraj Khanna, Santa Clara, CA (US)

(73) Assignee: KLA-Tencor Corporation, Milpitas, CA (US)

(*) Notice: Subject to any disclaimer, the term of this patent is extended or adjusted under 35 U.S.C. 154(b) by 0 days.

(21) Appl. No.: 13/557,047

(22) Filed: Jul. 24, 2012

(65) Prior Publication Data

US 2013/0048873 A1 Feb. 28, 2013

Related U.S. Application Data

(60) Provisional application No. 61/512,309, filed on Jul. 27, 2011, provisional application No. 61/531,227, filed on Sep. 6, 2011.

(51) Int. Cl.
*G01N 21/64* (2006.01)

(52) U.S. Cl.
USPC ..................................................... 250/459.1

(58) Field of Classification Search
USPC ..................................................... 250/459.1
See application file for complete search history.

(56) References Cited

U.S. PATENT DOCUMENTS

| | | | |
|---|---|---|---|
| 4,661,770 A | 4/1987 | von Roos | |
| 6,081,127 A | 6/2000 | Wagner et al. | |
| 7,919,762 B2 | 4/2011 | Trupke et al. | |
| 8,064,054 B2 | 11/2011 | Trupke et al. | |
| 2009/0051914 A1 | 2/2009 | Trupke et al. | |
| 2009/0206287 A1 | 8/2009 | Trupke et al. | |
| 2011/0025839 A1 | 2/2011 | Trupke et al. | |
| 2011/0117681 A1 | 5/2011 | Bardos et al. | |
| 2011/0188733 A1 | 8/2011 | Bardos et al. | |

FOREIGN PATENT DOCUMENTS

| | | | |
|---|---|---|---|
| JP | 2004006756 A | * | 1/2004 |
| RU | 1778821 A1 | | 11/1992 |
| RU | 2006987 C1 | | 1/1994 |

OTHER PUBLICATIONS

V. K. Khanna, "Physical understanding and technological control of carrier lifetimes in semiconductor materials and devices: A critique of conceptual development, state of the art and applications," 2005, Progress in Quantum Electronics, vol. 29, pp. 59-163.*

* cited by examiner

*Primary Examiner* — Kiho Kim
(74) *Attorney, Agent, or Firm* — Spano Law Group; Joseph S. Spano

(57) ABSTRACT

Methods and apparatus are presented to measure the photoluminescence of incoming wafers and extract parameters such as minority carrier life time, diffusion length, and defect density that may be used to predict final solar cell efficiency. In some examples, illumination light is supplied to a side of an as-cut silicon wafer and the induced luminescence measured from the same side and the opposite side of the wafer is used to determine an indication of the minority carrier lifetime. In another example, the luminescence induced by two instances of illumination light of different wavelength is used to determine an indication of the minority carrier lifetime. In another example, the spatial distribution of luminescence intensity over an area surrounding a focused illumination spot is used to determine an indication of the minority carrier lifetime. Other apparatus useful to passivate the surface of a wafer for inspection are also presented.

21 Claims, 17 Drawing Sheets

SOLAR METROLOGY METHODS AND APPARATUS

CROSS REFERENCE TO RELATED APPLICATIONS

The present application for patent claims priority under 35 U.S.C. §119 from U.S. provisional patent application Ser. No. 61/512,309, entitled "Solar Metrology Methods and Apparatus," filed Jul. 27, 2011, and from U.S. provisional patent application Ser. No. 61/531,227, entitled "Method and Apparatus for Predicting Solar Cell Wafer Efficiency," filed Sep. 6, 2011, the subject matter of which is incorporated herein by reference.

TECHNICAL FIELD

The described embodiments relate to inspection of components used in the manufacture of solar power generating devices, and more particularly to estimation of bulk carrier lifetime.

BACKGROUND INFORMATION

Semiconductor materials are a fundamental building block of many solar power generating devices. The quality of the semiconductor structures that comprise these devices is critical to their overall power generating efficiency. Minority carrier life time and the related minority carrier diffusion length within a semiconductor structure are parameters used to characterize the quality of a semiconductor material and predict solar cell efficiency.

The number of minority carriers in a material is increased above equilibrium by external excitation (e.g., absorption of photons). The excess minority carriers decay back to the equilibrium carrier concentration by recombination of electron-hole pairs. Minority carrier lifetime is the average time that a carrier spends in an excited state within a semiconductor material before recombination. Solar cell efficiency is related to the rate at which recombination occurs. Two parameters that are indicative of the recombination rate are the minority carrier lifetime and the minority carrier diffusion length.

Techniques exist to effectively measure minority carrier lifetime of solar cells late in the manufacturing process. Specifically, after the surfaces of a solar wafer have been passivated, techniques such as quasi-steady state photoconductance (QSSPC) and microwave-detected photoconductance decay (MW-PCD) can be used to measure the minority carrier lifetime. However, wafers entering the solar manufacturing process (i.e., "as-cut" wafers) have a large density of surface defects (i.e., dangling bonds) that dominate the electron-hole recombination process. These measurement techniques are unable to distinguish recombination events in the bulk of the semiconductor material from the relatively large number of recombination events at the surface. As a result, the measurements are dominated by surface defects that will be eliminated (e.g., by gettering and passivation) later on in the manufacturing process. In addition, photo-conductivity measurements have traditionally suffered from relatively low resolution and throughput capability.

Existing photoluminescence methods can generate high resolution full wafer images, but extracting relevant parameters demonstrating good correlation to final cell efficiency is difficult for similar reasons.

There is a need for effective measurement techniques to identify the minority carrier lifetime or diffusion length early in the manufacturing process to identify semiconductor structures that will not yield suitably efficient finished solar cells. More specifically, there is a need for measurement techniques that yield results indicative of the minority carrier lifetime or diffusion length in the bulk of an "as-cut" semiconductor material.

SUMMARY

Methods and apparatus for characterizing semiconductor wafers for solar cell manufacturing are presented. Specifically methods and apparatus to measure the photoluminescence of incoming wafers and extract parameters such as minority carrier life time, diffusion length, and defect density that can be used to predict final cell efficiency. Such measurements allow manufacturers to optimize manufacturing process based on incoming wafer quality to improve yield and lower manufacturing cost.

In one aspect, inspection system 100 supplies an illumination light to at least one side of an as-cut silicon wafer and determines an indication of the minority carrier lifetime or diffusion length in the bulk of the wafer based on photoluminescence measured from both the same side and the opposite side of the wafer the supplied illumination.

In one preferred embodiment, a light capture device is located on one side of a wafer. An illumination light is provided to the same side of the wafer as the light capture device. A portion of the resulting photoluminescence is captured by the light capture device. After completing the capture of the photoluminescence stimulated by the illumination on the same side as the light capture device, illumination light is provided to the side of the wafer opposite the light capture device. A portion of the resulting photoluminescence is captured by the light capture device. The ratio in luminous intensity between photoluminescence emitted on the same side of the wafer as the illumination light and photoluminescence emitted on the opposite side of the wafer is indicative of the minority carrier lifetime or diffusion length in the bulk of the wafer.

In another embodiment, an illumination light is provided to one side of the wafer. A light capture device is located on one side of the wafer and a second light capture device is located on the opposite side of the wafer. Each light capture device captures a portion of the resulting photoluminescence from both sides of the wafer, respectively. The ratio in luminous intensity between photoluminescence emitted on the same side of the wafer as the illumination light and photoluminescence emitted on the opposite side of the wafer is indicative of the minority carrier lifetime or diffusion length in the bulk of the wafer.

In another aspect, inspection system 100 supplies an illumination light to a wafer in at least two different instances. Each instance of the illumination light has a different peak wavelength. Inspection system 100 determines an indication of the minority carrier lifetime or diffusion length in the bulk of the wafer based on photoluminescence measured from the wafer in response to each different illumination instance.

In yet another aspect, inspection system 100 supplies an illumination light to a wafer over a focused illumination spot and images the photoluminescence emitted from the surface of the wafer over a larger area around the illumination spot. Inspection system 100 determines a spatial distribution of the luminous intensity of the photoluminescence. Based on the spatial distribution of the luminous intensity of the photoluminescence, inspection system 100 estimates a value of the minority carrier lifetime or diffusion length in the bulk of the wafer.

In some examples, this estimate of the minority carrier lifetime or diffusion length in the bulk of the wafer can be used to calibrate the indicators of the minority carrier lifetime or diffusion length in the bulk of the wafer determined by other methods described herein. For example, the ratio of photoluminescence intensity for two illumination instances each with a different peak wavelength provides an indication of the minority carrier lifetime or diffusion length in the bulk of the wafer relative to similar ratios taken over different areas of a wafer surface. These indications can be scaled by the estimated value of the minority carrier lifetime or diffusion length in the bulk of the wafer.

In some embodiments, the illumination spot is focused on the surface of the wafer. In some other embodiments, the illumination spot is focused to a location within the bulk of the wafer.

In yet another aspect, the surface of the wafer is passivated temporarily while undergoing inspection by any of the methods described herein. By passivating the surface of the wafer, electron-hole recombination at the surface can be reduced, allowing photons emitted from electron-hole recombination in the bulk of the wafer to be more visible in the light emitted at the wafer surface.

In some embodiments, an alternating electrical field is generated slightly above and below the wafer. The alternating electrical field may drive the minority carriers away from the wafer surface and toward the bulk of the wafer. In this manner, photons emitted from electron-hole recombination in the bulk of the wafer are more visible in the light emitted at the wafer surface.

In some other embodiments, an electrical charge is applied to the surface of the wafer that may drive the minority carriers away from the wafer surface and toward the bulk of the wafer. In this manner, photons emitted from electron-hole recombination in the bulk of the wafer are more visible in the light emitted at the wafer surface.

In some other embodiments, a magnetic field is applied in the plane of the wafer. The applied magnetic field may drive the minority carriers toward the center of the wafer. In this manner, photons emitted from electron-hole recombination in the bulk of the wafer are more visible in the light emitted at the wafer surface. In some embodiments, the magnetic field is generated by a permanent magnet. In some other embodiments, the magnetic field is induced by an oscillating current flow through a coil enveloping the wafer.

In some other embodiments, a micro chemical processor delivers passivation fluids to the surface of the wafer and subsequently evacuates the fluids from the wafer surface after a predetermined period of time. Exemplary passivation chemicals include iodine and solvent mixtures. Chemical reaction between the passivation fluids and the wafer surface may passivate the wafer surface. In this manner, photons emitted from electron-hole recombination in the bulk of the wafer are more visible in the light emitted at the wafer surface.

In some embodiments, inspection system 100 implements the methods of estimating the minority carrier lifetime or diffusion length in the bulk of the wafer described herein in any of a spot mode, a line mode, or over the entire wafer.

In some embodiments, inspection system 100 implements any combination of the methods of estimating the minority carrier lifetime or diffusion length in the bulk of the wafer described herein.

The foregoing is a summary and thus contains, by necessity, simplifications, generalizations and omissions of detail; consequently, those skilled in the art will appreciate that the summary is illustrative only and is not limiting in any way.

Other aspects, inventive features, and advantages of the devices and/or processes described herein will become apparent in the non-limiting detailed description set forth herein.

DETAILED DESCRIPTION

Reference will now be made in detail to background examples and some embodiments of the invention, examples of which are illustrated in the accompanying drawings.

Figure 1:
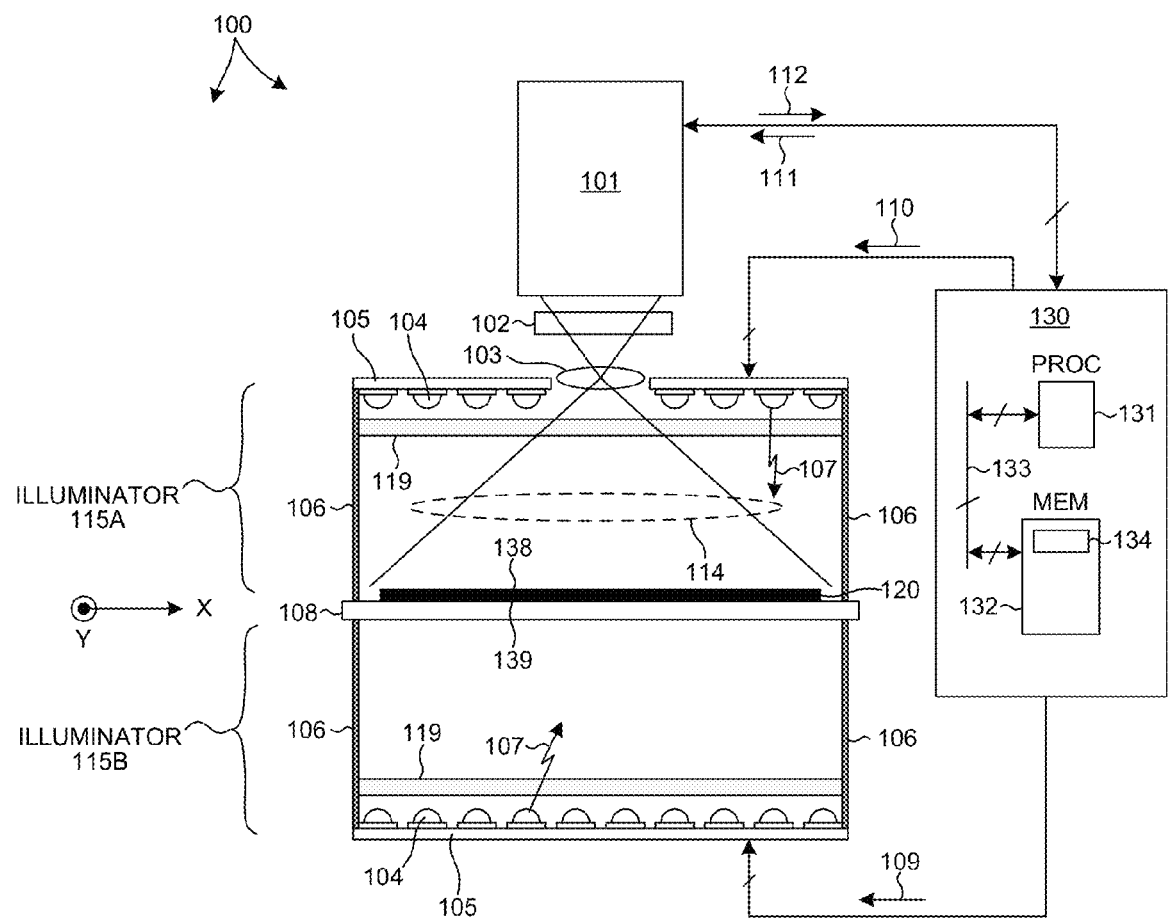
FIG. 1 is a simplified diagram illustrative of one embodiment of an inspection system 100 that may be used to perform the inspection method 200 described herein.

FIG. 1 is a simplified schematic view of one embodiment of an inspection system 100 that may be used to perform the inspection methods described herein. For simplification, some optical components of the system have been omitted. By way of example, folding mirrors, beam forming optics, polarizers, additional light sources, additional spectral filters, and additional light capture devices may also be included. All such variations are within the scope of the invention described herein. The inspection system described herein may be used for inspecting solar films, as well as semiconductor wafers.

As illustrated in FIG. 1, inspection system 100 includes a light capture device 101, a controller 130, a top side illuminator 115A and a bottom side illuminator 115B, and a specimen 120 under inspection. Each illuminator 115 includes a light source 104. As illustrated the light source of illuminators 115A and 115B is a number of high power LEDs 104. LEDs are mounted to a mounting board 105 that electrically interconnects each LED 104 to a source of power. When powered, LEDs 104 emit illumination light 107 that is directed to specimen 120 by the illuminator 115. As illustrated, illuminator 115 includes reflective sidewalls 106 that direct light emitted from the LEDs 104 to wafer 120. Reflective sidewalls 106 may be specular reflective or diffuse reflective as required to efficiently and homogeneously illuminate the surfaces 138 and 139 of specimen 120. Illuminators 115A and 115B also include a spectral filter to block radiation from the LEDs 104 that is in the wavelength range of photoluminescence of the wafer 120. Although, the radiation from the LEDs does not include a substantial component within the wavelength range of photoluminescence of the wafer 120, it can be a significant noise contributor in photoluminescence detection. In some examples, the spectral filters 119 are short pass filters with a cut-off wavelength below one micrometer. In general spectral filters 119 are placed in the light path between the light source and wafer 120. As illustrated, the spectral filters 119 are located close to the LEDs 104 and in the path of light emission from LEDs 104. In some embodiments, spectral filter 119 may be a single element that covers all of the LEDs 104 of an illuminator 115. In some other embodiments, spectral filter 119 may include a number of elements, each in the path of light emission for one or more LEDs 104. In some embodiments, the spectral filter 119 is included as part of an integrated LED package. In this manner, the light emitted from LEDs 104 is already substantially free of radiation above the desired cut-off wavelength. Spectral filter 119 is illustrated in FIG. 1 by way of example, and in general, may be applied to any of the embodiments described herein.

Although, as illustrated, illuminators 115 are configured as mirror boxes driven by LED light sources, any other illuminator may be employed. By way of non-limiting example, illuminator 115 may include a laser, a diode laser, a helium neon laser, an argon laser, a solid state laser, a diode pumped solid state (DPSS) laser, a xenon arc lamp, a gas discharging lamp, or an incandescent lamp as a light source. The light source may be configured to emit near monochromatic light or broadband light. In general, the illumination subsystem is configured to direct light having a wavelength band that is readily absorbed by the semiconductor material (e.g., light having a wavelength range between 600 nanometers and 1.1 micrometers). Therefore, if the light source is a broadband light source, the illuminator may also include one or more spectral filters that may limit the wavelength of the light directed to the specimen. The one or more spectral filters may be bandpass filters and/or edge filters and/or notch filters. Similarly, illuminator 115 includes optical elements that generate a desired incident illumination distribution on a surface of wafer 120.

In addition to the light sources described herein, other types of excitation sources may be considered, including electrical sources (e.g., a voltage or current source), or a combination of light and electrical sources. In the embodiments described herein, the illuminator 115 generates light suitable for inducing photoluminescence in specimen 120. However, electrical excitation sources may also be considered, alternatively, or in combination with light sources to stimulate electroluminescence, alone, or in combination with photoluminescence. The methods described herein may also be applied to a specimen undergoing electroluminescence as well as photoluminescence.

As illustrated in FIG. 1, specimen 120 is a thin, planar semiconductor wafer with a top side 138 and a bottom side 139, opposite the top side. Wafer 120 may be a bare wafer (e.g., unprocessed silicon) or a partially processed solar cell. In the embodiment illustrated in FIG. 1, illuminators 115A-B supply incident illumination to surfaces 138 and 139, respectively of specimen 120. In response, specimen 120 undergoes photoluminescence and emits light from its surfaces.

System 100 includes collection optics 103 to collect the light emitted from the surface of wafer 120 and focus that light onto light capture device 101. The output of light capture device 120 is supplied to controller 130 for processing the signals and determining an indication of the bulk carrier lifetime of a portion of wafer 120 under inspection. An image of an area under inspection can be obtained by arrangement of the output signals 112 of each light capture device 101 stored in a memory 132 of controller 130.

Collection optics 103 may be a lens, a compound lens, or any appropriate lens known in the art. Alternatively, any of collection optics 103 may be a reflective or partially reflective optical component, such as a mirror. In addition, it is to be understood that the collection optics may be arranged at any appropriate collection angle. The collection angle may vary depending upon, for example, the angle of incidence and/or topographical characteristics of the specimen.

System 100 includes one or more light capture devices 101. A light capture device 101 generally functions to convert the emitted light into an electrical signal, and therefore, may include substantially any photodetector known in the art. However, a particular detector may be selected for use within one or more embodiments of the invention based on desired performance characteristics of the detector, the type of specimen to be inspected, and the configuration of the illumination. For example, if the amount of light available for inspection is relatively low, an efficiency enhancing detector such as a time delay integration (TDI) camera may increase the signal-to-noise ratio and throughput of the system. However, other detectors such as charge-coupled device (CCD) cameras, photodiodes, phototubes and photomultiplier tubes (PMTS) may be used, depending on the amount of light available for inspection and the type of inspection being performed. In at least one embodiment of the invention, a CCD camera is used for detecting light emitted from wafer 120. The term "single detector" is used herein to describe a detector having only one sensing area, or possibly several sensing areas (e.g., a detector array or multi-anode PMT). Regardless of number, the sensing areas of a single detector are embodied within a single enclosure.

System 100 may also include a filter 102 to reduce the spectral content of the photoluminescence. Exemplary filters include low-pass filters, high-pass filters, band-pass filters, edge filters, and notch filters. Filter 102 is illustrated as a discrete hardware component, but may also be implemented as part of light capture device 101. One or more filter components 102 may be applied to collected luminescence 114. However, filtering may also be implemented by execution of software by controller 130.

System 100 also includes various electronic components (not shown) needed for processing the signals detected by detector(s) of light capture device 101. For example, system 100 may include amplifier circuitry to receive output signals 112 of light capture device 101 and to amplify those output signals by a predetermined amount and an analog-to-digital converter (ADC) to convert the amplified signals into a digital format suitable for use by processor 131.

In the embodiment illustrated in FIG. 1, wafer 120 is supported by a wafer chuck 108. To facilitate illumination of wafer 120 from both sides, wafer chuck 108 is constructed from an optically transparent material (e.g., glass). Wafer chuck 108 is moved, for example, in the x and y directions indicated in FIG. 1, by a wafer positioning system (not shown). A wafer positioning system moves wafer 120 under inspection to any desired position within inspection system 100.

In addition, inspection system 100 may include peripheral devices useful to accept inputs from an operator (e.g., keyboard, mouse, touchscreen, etc.) and display outputs to the operator (e.g., display monitor). By way of example, input commands from an operator may be used by processor 131 to adjust inspection areas of wafer 120. Also, by way of example, luminous intensity images of wafer 120 may be presented to an operator on a display monitor.

In the depicted embodiments, controller 130 includes a processor 131 and memory 132 and implements inspection control functionality of inspection system 100 in accordance with the methods described herein. Hence, in some embodiments, controller 130 is a dedicated controller, however, in other embodiments, inspection control functionality may be implemented by any other general purpose computer or dedicated hardware of inspection system 100 configured to operate in an analogous manner.

As depicted in FIG. 1, controller 130 receives signals 112 from light capture device 101. Signals 112 are indicative of the intensity of photoluminescence captured from a surface of wafer 120. Controller 130 may also communicate command signals 111 to light capture device 101, command signals 109 to illuminator 115B, and command signals 110 to illuminator 115A. For example, controller 130 may synchronize the light capture sequence of light capture device 101 with the illumination provided by either or both of illuminators 115A and 115B. In this manner, controller 130 controls the inspection of wafer 120.

The luminescence induced in wafer 120 is captured with a luminescence capture device 101. The embodiments and methods described herein may be applied to image portions of arbitrary size. In some examples, imaging or mapping techniques may be applied to spatially resolve the luminescence emitted from the surface of the wafer 120. In one example, the luminescence capture device 101 is an imaging device comprising an array with more than one individual sensor (e.g., charge coupled device (CCD) camera or another pixel based detector). Each pixel collects the luminescence from a limited area on the wafer 120, thereby creating an image of the wafer surface. In another example, the imaging device includes a focusing element and a focal plane array of light-sensitive electronic elements. The focal plane array may be made of silicon and may be cooled to improve the signal-to-noise ratio. The focal plane array of light-sensitive electronic elements may be a CCD array. In some examples, the focal plane array of light sensitive electronic elements may be made from InGaAs. However, as described herein, other devices may be practiced without departing from the scope of the invention.

Figure 14:
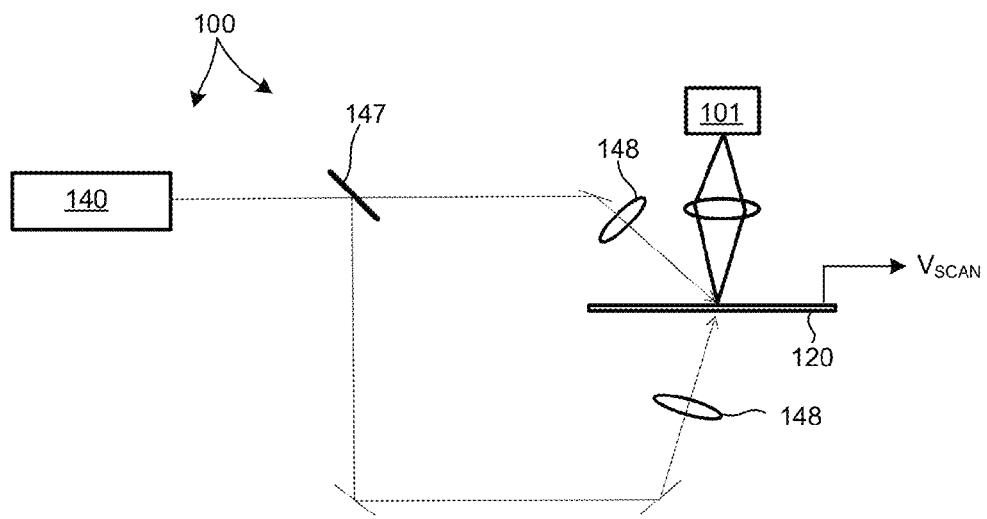
FIG. 14 is a simplified diagram illustrative of another embodiment of an inspection system 100 that may be used to perform the inspection method 200 described herein.
Figure 15:
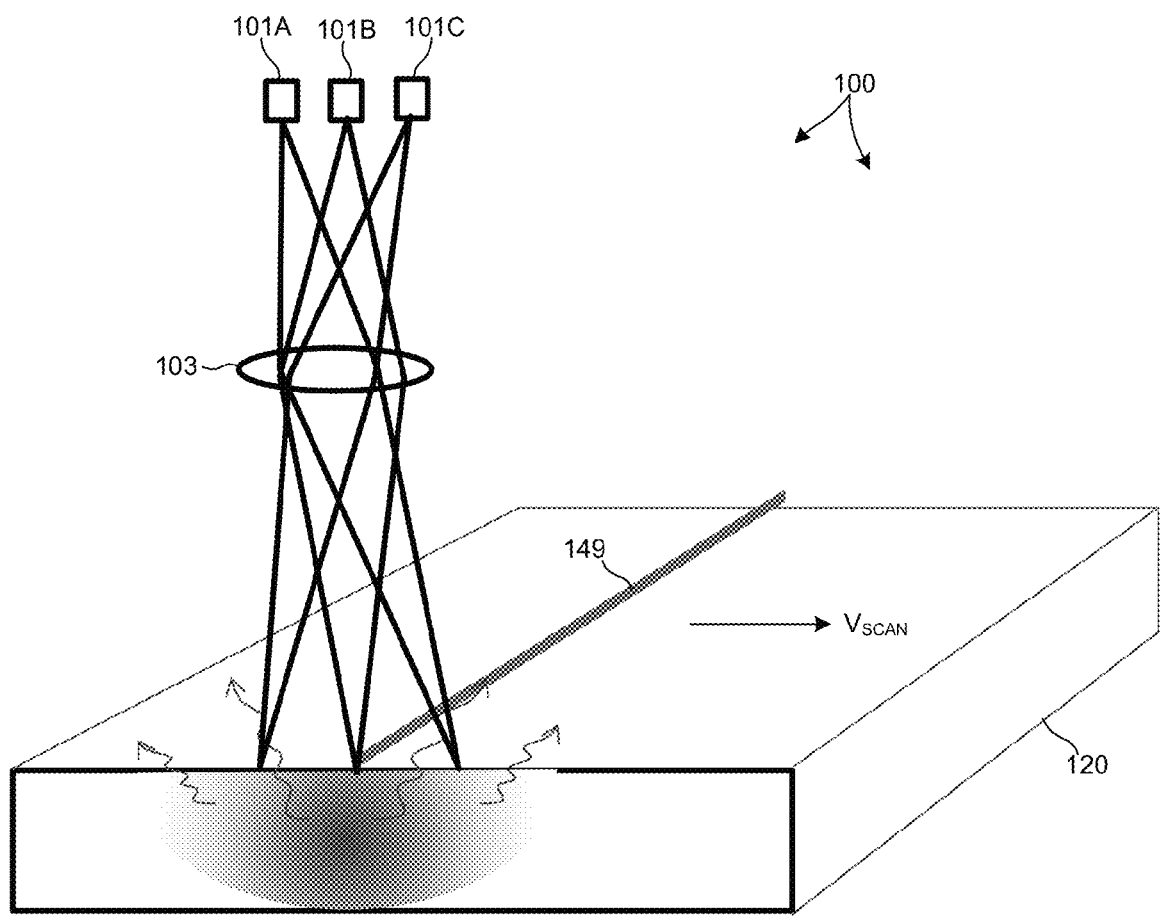
FIG. 15 is a simplified diagram illustrative of another embodiment of an inspection system 100 that may be used to perform the inspection method 220 described herein.

In a mapping technique, a single detector collects luminescence from a limited area of the wafer (e.g., over a spot or a line). A wafer stage moves the wafer 120 relative to the detection system to obtain a map of the luminescence intensity. For example, as illustrated in FIGS. 14 and 15, illumination is provided to wafer 120 over a line area 149. Wafer 120 is translated in a direction perpendicular to the length of the line area 149. A single line camera may be employed (as illustrated in FIG. 14) or multiple line cameras (e.g., line cameras 101A-C illustrated in FIG. 15) may be employed. In the embodiment depicted in FIG. 14, a laser illumination source 140 is directed, alternatively, to both the top and bottom surfaces of wafer 120 by beam switching element 147. Line focus optics 148 shape the light emitted from laser illumination source 140 to line area 149 on wafer 120. The embodiments illustrated in FIGS. 14 and 15 may be employed to implement the methods described herein.

In some embodiments, a large area detector is used to obtain spatially averaged intensities over the surface of the wafer. The intensities may be averaged over the entire wafer or over any portion of a wafer surface. Exemplary large area detectors include a Silicon photodiode, a Germanium photodiode, an InGaAs Photodiode or a HgCdTe photodiode.

In one aspect, inspection system 100 supplies an illumination light to at least one side of an as-cut silicon wafer and determines an indication of the minority carrier lifetime or diffusion length in the bulk of the wafer based on photoluminescence measured from both the same side and the opposite side of the wafer as the supplied illumination.

Figure 21:
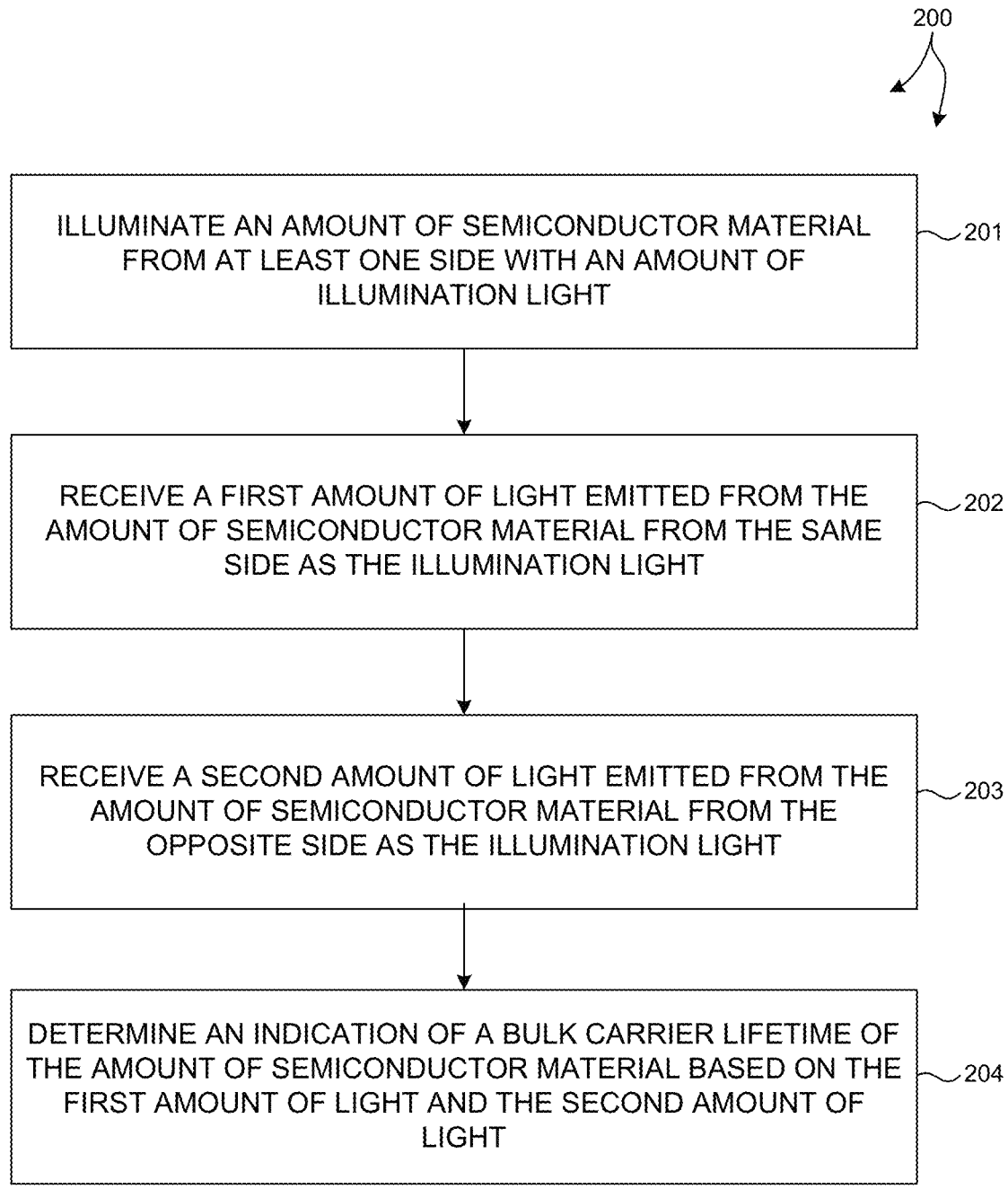
FIG. 21 is a flowchart illustrative of a method 200 of measuring the photoluminescence of an incoming wafer and determining an indication of the minority carrier lifetime or diffusion length in the bulk of the wafer.

FIG. 21 is a flowchart illustrative of a method 200 of measuring the photoluminescence of an as-cut wafer from both the same side and the opposite side of the wafer as a supplied illumination and determining an indication of the minority carrier lifetime or diffusion length in the bulk of the wafer based on the measured photoluminescence.

By way of non-limiting example, method 200 will be discussed with reference to the embodiment of inspection system 100 depicted in FIG. 1.

In block 201, inspection system 100 illuminates an amount of semiconductor material from at least one side with an illumination light. As illustrated in FIG. 1, illuminator 115A is configured to illuminate the top surface 138 of wafer 120 and illuminator 115B is configured to illuminate the bottom surface of wafer 120. In one example, controller 130 communicates a command signal 110 to illuminator 115A to illuminate the top surface 138 of wafer 120. In response, illuminator 115A supplies illumination light 107 from LEDs 104 to the top surface 138 of wafer 120 for a period of time specified by controller 130.

Figure 6:
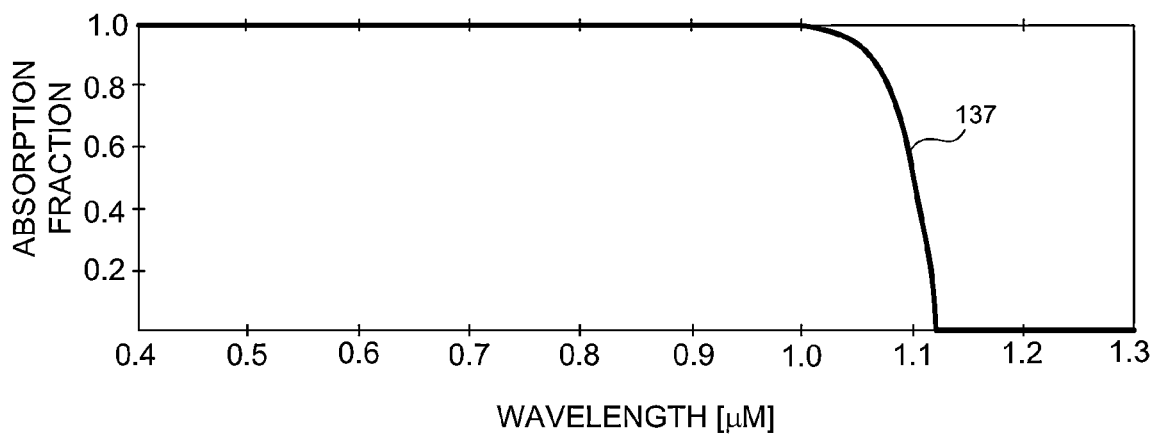
FIG. 6 is a plot illustrative of the fraction of incident light absorbed by a silicon wafer of 200 micrometers thickness as a function of wavelength of the incident light.

Illumination light 107 may be any wavelength, but a peak wavelength below 1.1 micrometers is preferred for the inspection of silicon wafers for at least two reasons. First, light with a wavelength above 1.1 micrometers tends to pass through silicon without absorption, effectively wasting the illumination light. Plotline 137 of FIG. 6 illustrates the absorption fraction of light through a silicon wafer of 200 micrometer thickness. As illustrated, light with a wavelength less than approximately one micrometer is completely absorbed by the wafer. However, light with a wavelength above approximately 1.125 micrometers passes through the wafer without any absorption. Second, reflected illumination light detected by light capture device 101 near the band-band transition of silicon (approximately 1.125 micrometers) contaminates the measurement of photoluminescence from the silicon wafer 120. Without significant spectral separation between the illumination light and the photoluminescence, the reflected illumination light cannot be effectively filtered out of the light detected by light capturing device 101. For these reasons, it is preferable to supply illumination light 107 to the surface of wafer 120 with a peak wavelength below 1.1 micrometers. In some examples, illumination light 107 has a peak wavelength between 400 nanometers and 1000 nanometers. In this manner, reflected illumination light can be filtered by filter 102 and contamination of the measurement of photoluminescence from the silicon wafer 120 by light capture device 101 can be avoided.

In block 202, inspection system 100 receives a first amount of luminescence emitted from the semiconductor material from the same side as the illumination light. As illustrated in FIG. 1, light capture device 101 is configured to collect luminescence 114 emitted from the top surface 138 of wafer 120. In one example, controller 130 transmits a command signal 111 to light capture device 101 to trigger the collection of light in synchronization with the illumination provided by illuminator 115A. Light capture device 101 transmits data signals 112 indicative of the luminescence intensity of the photoluminescence emitted from the top surface 138 of wafer 120 as detected by light capture device 101. Controller 130 records the image in memory 132.

Subsequently, controller 130 communicates a command signal 109 to illuminator 115B to illuminate the bottom surface 139 of wafer 120. In response, illuminator 115B supplies illumination light 107 from LEDs 104 of illuminator 115B to the bottom surface 139 of wafer 120 for a period of time specified by controller 130.

In block 203, inspection system 100 receives a second amount of luminescence emitted from the semiconductor material from the opposite side as the illumination light. As illustrated in FIG. 1, light capture device 101 is configured to collect luminescence 114 emitted from the top surface 138 of wafer 120 based on illumination light provided to the bottom surface 139 of wafer 120. In one example, controller 130 transmits a command signal 111 to light capture device 101 to trigger the collection of light in synchronization with the illumination provided by illuminator 115B. Light capture device 101 transmits data signals 112 indicative of the luminescence intensity of the photoluminescence emitted from the top surface 138 of wafer 120 as detected by light capture device 101. Controller 130 records the image in memory 132.

In block 204, inspection system 100 determines an indication of the bulk carrier lifetime or the bulk carrier diffusion length based on the luminescence received from the same side and the opposite side of the illumination light. In one example, controller 130 calculates the difference between the image of luminescence intensity of the wafer with same side illumination and the image of luminescence intensity of the wafer with opposite side illumination as the indication of the bulk carrier lifetime or the bulk carrier diffusion length. In another example, controller 130 calculates the ratio between the image of luminescence intensity of the wafer with same side illumination and the image of luminescence intensity of the wafer with opposite side illumination as the indication of the bulk carrier lifetime or the bulk carrier diffusion length.

Figure 3:
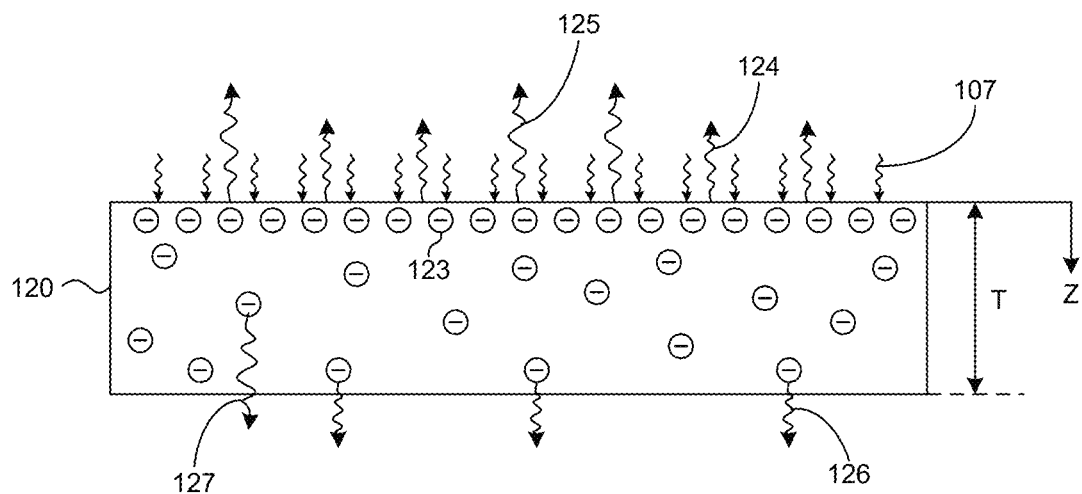
FIG. 3 is a simplified diagram illustrative of electron-hole generation, minority carrier diffusion, and electron-hole recombination in silicon in accordance with method 200 as described herein.
Figure 4:
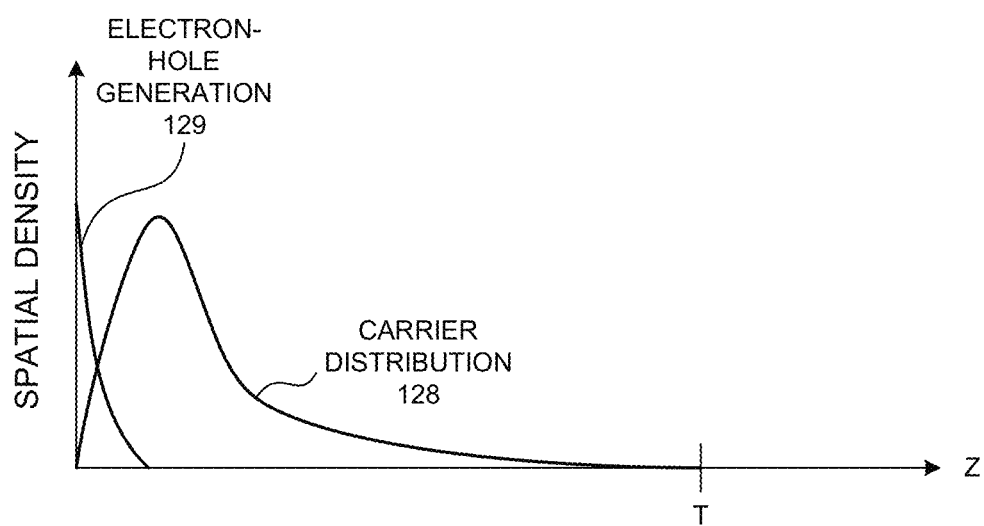
FIG. 4 is a simplified diagram illustrative of an exemplary spatial distribution of generated electron-holes and carriers during inspection.
Figure 5:
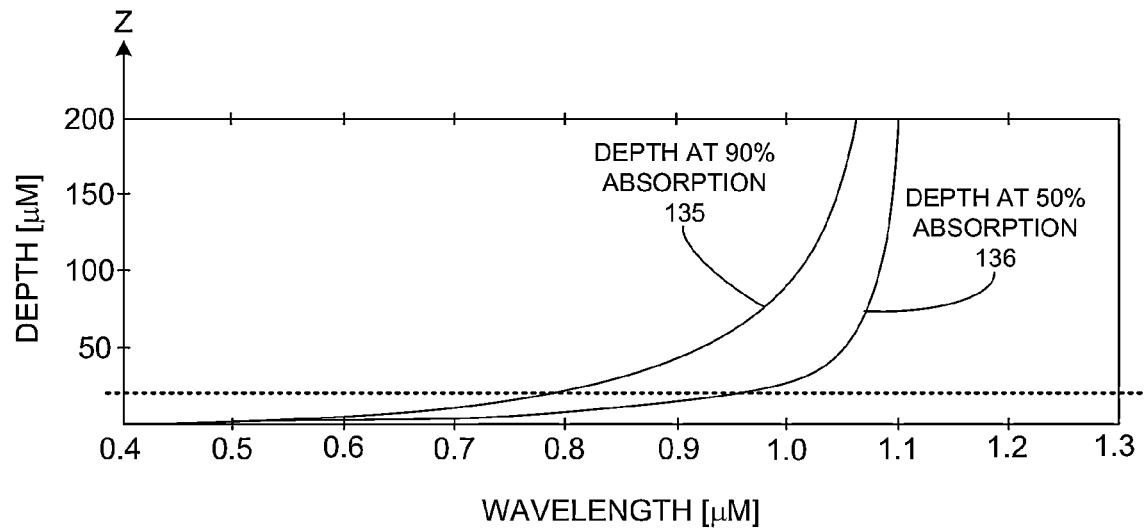
FIG. 5 is a plot illustrative of the depths at which 50% and 90% of light incident on silicon is absorbed as a function of the wavelength of the incident light.

As illustrated in FIG. 3, illumination light 107 generates electron-hole pairs very near the surface of wafer 120 being illuminated. As illustrated by plotline 129 of FIG. 4, the density of generated electron-holes is highest near the illuminated surface of wafer 120 and rapidly drops off through the thickness, T, of wafer 120. In addition, FIG. 5 illustrates the depth into a silicon wafer of 200 micrometers thickness where absorption reaches 50% (plotline 136) and 90% (plotline 135) as a function of wavelength of light. As illustrated in FIG. 5, at a depth of 20 micrometers, light below a wavelength of 950 nanometers is already 50% absorbed and is 90% absorbed within approximately 60 micrometers.

Figure 2:
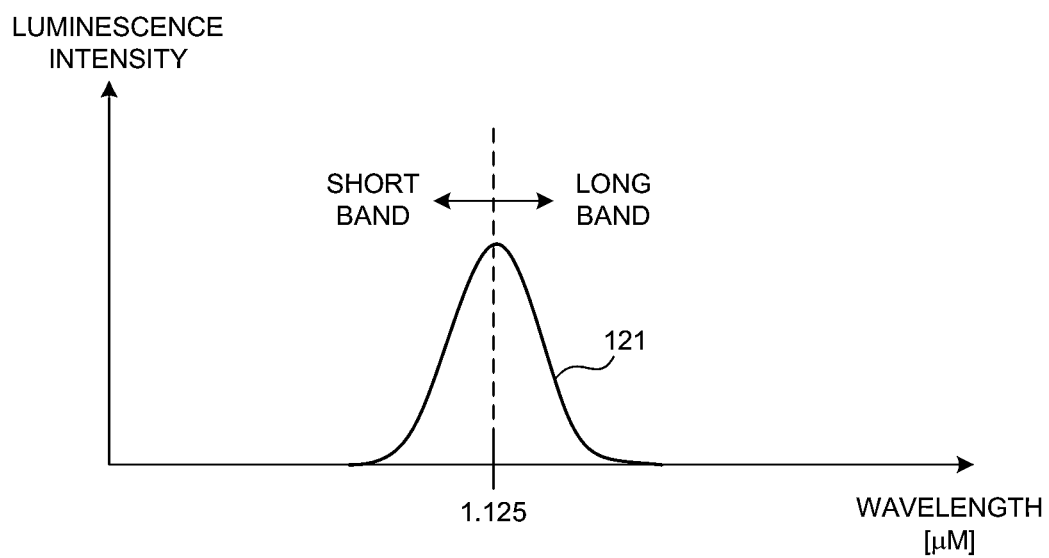
FIG. 2 is a simplified diagram illustrative of the wavelength distribution of photoluminescence of silicon.

After electron-hole generation, the resulting minority carriers 123 begin to diffuse within wafer 120. The carriers distribute themselves through the thickness, T, for example, as illustrated by plotline 128 of FIG. 4. The high density of surface defects in as-cut wafers reduces the minority carrier concentration near the surface. The photoluminescence light is distributed over a wavelength band as illustrated in FIG. 2. The peak luminescence intensity is centered on the band-band transition wavelength of the silicon material. photoluminescence emission with a higher wavelength than the band-band transition wavelength may be termed long band photoluminescence. photoluminescence emission with a lower wavelength than the band-band transition wavelength may be termed short band photoluminescence. FIG. 3 illustrates both long band emission 125 and short band emission 124 from wafer 120. Some minority carriers migrate into the wafer thickness and recombine with majority carriers in the bulk of wafer 120. Other carriers migrate completely across the wafer thickness and recombine at the opposite surface. As the minority carrier lifetime or diffusion length in the bulk of the wafer increases, there are more minority carriers that migrate farther away from the surface and generate photoluminescence deeper inside the bulk of wafer 120. At the same time, a portion of the generated photoluminescence is re-absorbed by the bulk of the wafer. The portion of the generated photoluminescence that is reabsorbed depends on the depth inside the wafer wherein the photoluminescence is generated and the wavelength of the photoluminescence. As the depth of the generated photoluminescence increases and the wavelength of the photoluminescence decreases, the likelihood is higher that a greater portion of the generated photoluminescence is re-absorbed. For this reason the ratio or the difference between luminescence intensity of the wafer with same side illumination and luminescence intensity of the wafer with opposite side illumination is indicative of the bulk carrier lifetime or the bulk carrier diffusion length.

As discussed, photoluminescence of the minority carriers includes both short band and long band emission. With reference to FIG. 5, long band emission (e.g., >1.125 micrometers) generally passes through wafer 120 without absorption. Thus, long band emission collected from the wafer surface could have originated from any location within wafer 120 with minimal likelihood of absorption. However, short band emission has a significantly higher likelihood of being absorbed as the path to the surface of wafer 120 increases. For example, if a minority carrier recombines in the middle of a wafer 120 of 200 micrometers thickness and emits photoluminescence with a 1.0 micrometer wavelength, the likelihood is greater than 90% than the photoluminescence is absorbed before reaching the surface of the wafer. As a result, the presence of short band photoluminescence at either the same side or opposite side of the illumination light indicates that the location of the recombination that gave rise to that photoluminescence was relatively close to the same or opposite surface of the wafer, respectively. Thus, in addition to taking the ratio or the difference between luminescence intensity of the wafer with same side illumination and luminescence intensity of the wafer with opposite side illumination, the luminescence intensity may be filtered to separate short band photoluminescence indicative of minority carriers that have traversed almost all the way across the thickness of the wafer.

In the preferred embodiment depicted in FIG. 1, a light capture device is located on one side of a wafer. An illumination light is provided to the same side of the wafer as the light capture device. A portion of the resulting photoluminescence is captured by the light capture device. After completing the capture of the photoluminescence stimulated by the illumination on the same side as the light capture device, illumination light is provided to the side of the wafer opposite the light capture device. A portion of the resulting photoluminescence is captured by the same light capture device.

In another embodiment, an illumination light is provided to one side of the wafer. A light capture device located on the same side of the wafer captures a portion of the photoluminescence stimulated by the illumination on the same side as the illumination source. In addition, a second light capture device is located on the opposite side of the wafer. The second light capture device captures a portion of the stimulated photoluminescence on the opposite side as the illumination source. Thus, each light capture device captures a portion of the photoluminescence from both sides of the wafer that was stimulated by an illumination light provided on one side only. This capture may occur simultaneously or sequentially. The embodiment illustrated in FIG. 1 is preferred because of the relatively low cost of an illuminator compared to that of a light capturing device.

In another aspect, inspection system 100 supplies an illumination light to a wafer in at least two different instances. Each instance of the illumination light has a different peak wavelength. Inspection system 100 determines an indication of the minority carrier lifetime or diffusion length in the bulk of the wafer based on photoluminescence measured from the wafer in response to each different illumination instance.

Figure 22:
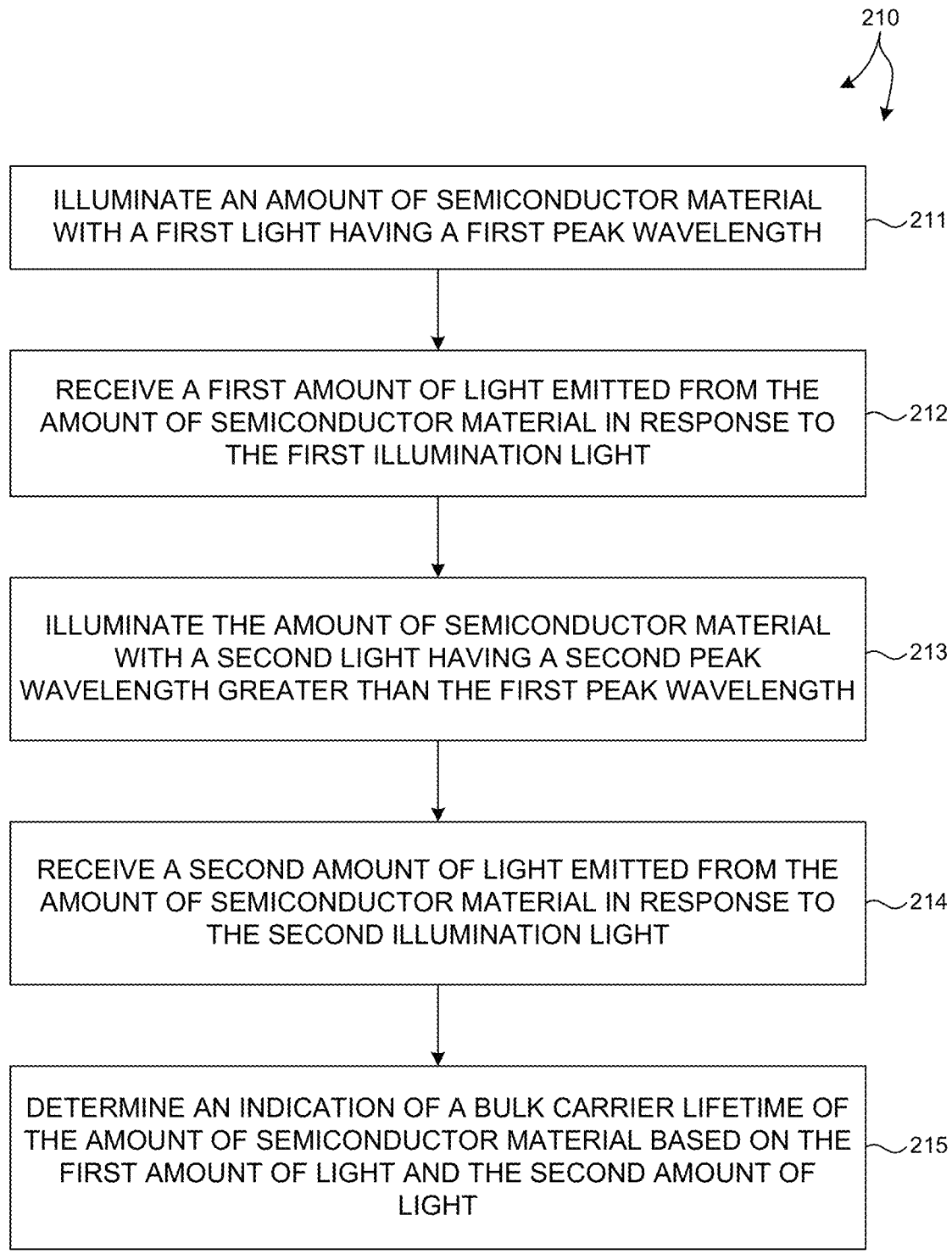
FIG. 22 is a flowchart illustrative of a method 210 of measuring the photoluminescence of an incoming wafer and determining an indication of the minority carrier lifetime or diffusion length in the bulk of the wafer.

FIG. 22 is a flowchart illustrative of a method 210 of sequentially measuring the photoluminescence of an as-cut wafer with illumination light of different wavelengths determining an indication of the minority carrier lifetime or diffusion length in the bulk of the wafer based on the measured photoluminescence.

Figure 7:
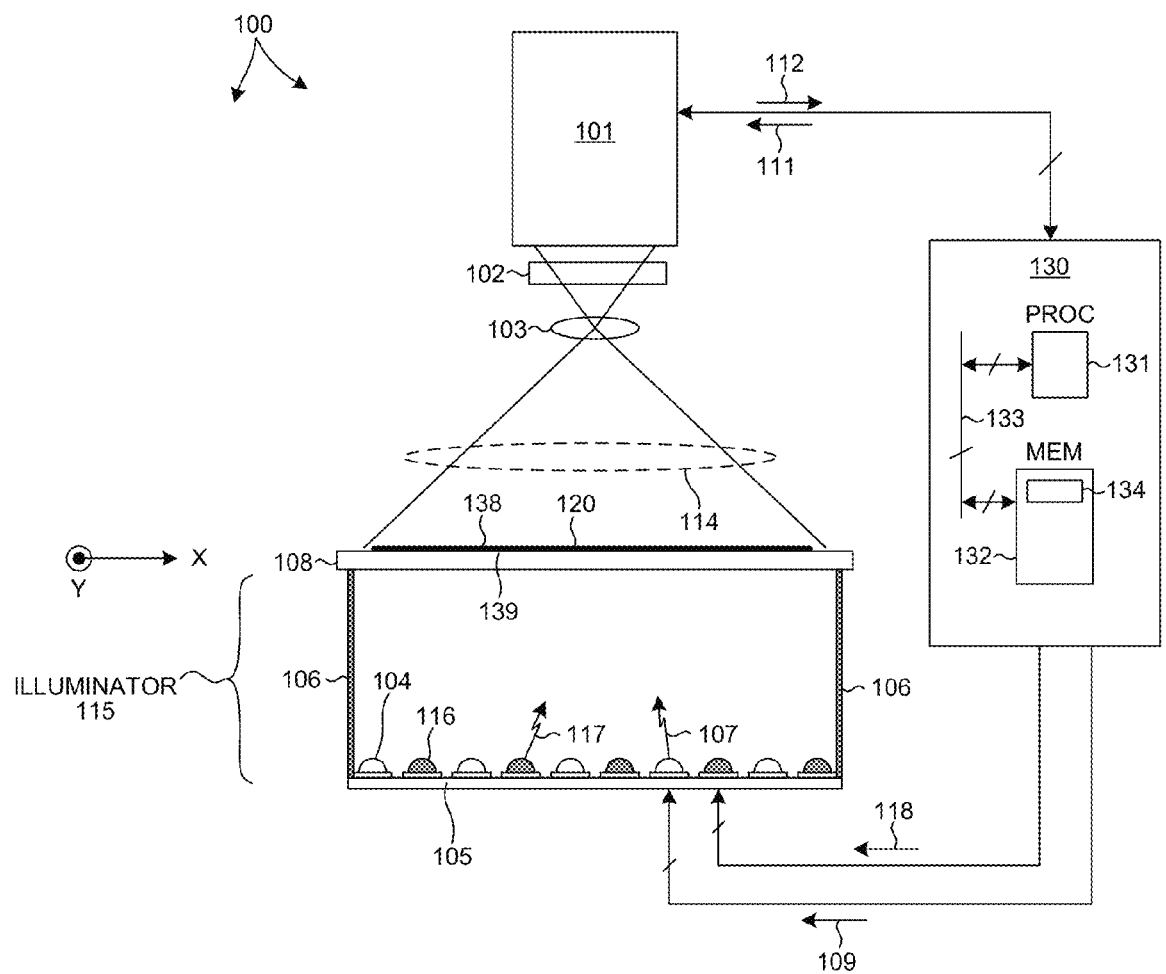
FIG. 7 is a simplified diagram illustrative of another embodiment of an inspection system 100 that may be used to perform the inspection method 210 described herein.

By way of non-limiting example, method 210 will be discussed with reference to the embodiment of inspection system 100 depicted in FIG. 7.

In block 211, inspection system 100 illuminates an amount of semiconductor material with an illumination light with a first peak wavelength. As illustrated in FIG. 7, illuminator 115 is configured to illuminate the bottom surface 139 of wafer 120. In one example, controller 130 communicates a command signal 109 to illuminator 115 to illuminate the bottom surface 139 of wafer 120. In response, illuminator 115 supplies illumination light 107 from LEDs 104 to the bottom surface 139 of wafer 120 for a period of time specified by controller 130. LEDs 104 are configured to collectively provide illumination 107 with a first peak wavelength.

As discussed hereinbefore, illumination light 107 may be any wavelength, but a peak wavelength below 1.1 micrometers is preferred. In one example, illumination light 107 has a peak wavelength between 600 nanometers and 1000 nanometers.

In block 212, inspection system 100 receives a first amount of luminescence emitted from the semiconductor material in response to the first illumination light. As illustrated in FIG. 7, light capture device 101 is configured to collect luminescence 114 emitted from the top surface 138 of wafer 120. In one example, controller 130 transmits a command signal 111 to light capture device 101 to trigger the collection of light in synchronization with the illumination light 107 provided by illuminator 115. Light capture device 101 transmits data signals 112 indicative of the luminescence intensity of the photoluminescence emitted from the top surface 138 of wafer 120 as detected by light capture device 101 in response to illumination light 107. Controller 130 records the image in memory 132.

In block 213, inspection system 100 illuminates the amount of semiconductor material with an illumination light with a second peak wavelength that is greater than the first peak wavelength. As illustrated in FIG. 7, illuminator 115 is configured to illuminate the bottom surface 139 of wafer 120. In one example, controller 130 communicates a command signal 118 to illuminator 115 to illuminate the bottom surface 139 of wafer 120. In response, illuminator 115 supplies illumination light 117 from LEDs 116 to the bottom surface 139 of wafer 120 for a period of time specified by controller 130. LEDs 116 are configured to collectively provide illumination light 117 with the second peak wavelength.

Illumination light 117 may be any wavelength, but a peak wavelength below 1.1 micrometers is preferred as discussed hereinbefore. In one example, illumination light 117 has a peak wavelength between 700 nanometers and 1.1 micrometers. In some examples, the difference in peak wavelength between illumination light 107 and illumination light 117 is at least 50 micrometers. In some other examples, the difference in peak wavelength between illumination light 107 and illumination light 117 is at least 100 micrometers. In some other examples, the difference in peak wavelength between illumination light 107 and illumination light 117 is at least 200 micrometers.

In block 214, inspection system 100 receives a second amount of luminescence emitted from the semiconductor material in response to the second illumination light. As illustrated in FIG. 7, light capture device 101 is configured to collect luminescence 114 emitted from the top surface 138 of wafer 120 in response to illumination light 117. In one example, controller 130 transmits a command signal 111 to light capture device 101 to trigger the collection of light in synchronization with the illumination light 117 provided by illuminator 115. Light capture device 101 transmits data signals 112 indicative of the luminescence intensity of the photoluminescence emitted from the top surface 138 of wafer 120 as detected by light capture device 101 in response to illumination light 117. Controller 130 records the image in memory 132.

In block 215, inspection system 100 determines an indication of the bulk carrier lifetime or the bulk carrier diffusion length based on the luminescence received from the wafer in response to the first amount of illumination light and the luminescence received from the wafer in response to the second amount of illumination light. In one example, controller 130 calculates the difference between the luminescence intensity of the wafer in response to each different illumination light. This difference is the indication of the bulk carrier lifetime or the bulk carrier diffusion length. In another example, controller 130 calculates the ratio between the luminescence intensity of the wafer in response to each different illumination light. This ratio is the indication of the bulk carrier lifetime or the bulk carrier diffusion length.

As discussed, the photoluminescence response to two instances of illumination light of different wavelength is the basis for an indication of the bulk carrier lifetime or the bulk carrier diffusion length. However, in general, more than two instances of illumination light of different wavelengths may be used as the basis for an indication of the bulk carrier lifetime or the bulk carrier diffusion length.

Figure 8:
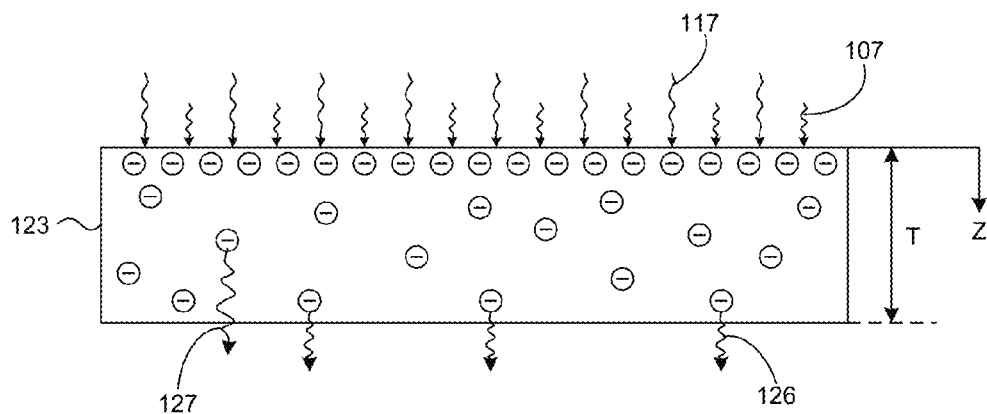
FIG. 8 is a simplified diagram illustrative of electron-hole generation, minority carrier diffusion, and electron-hole recombination in silicon in accordance with method 210 as described herein.

As illustrated in FIG. 8, both illumination light 107 and 117 generate electron-hole pairs in silicon wafer 120. However, as illustrated in FIG. 5, the depth of penetration into a silicon wafer of 200 micrometers thickness depends on the wavelength of light. Thus, for an illumination instance of relatively long wavelength illumination light (e.g., 900 nanometers) one can expect a distribution of electron-hole generation 129 (see FIG. 4) that extends deeper into the wafer 120 than an illumination instance of relatively short wavelength illumination (e.g., 800 nanometers).

After electron-hole generation for each illumination instance, the resulting minority carriers 123 begin to diffuse within wafer 120. Some minority carriers migrate into the wafer thickness and recombine at a defect in the bulk of wafer 120. Other carriers migrate from the bulk of the wafer 120 toward the surface of the wafer and recombine near the surface where their photoluminescence is captured by light capturing device 101. For electron-holes generated by longer wavelength illumination light, the minority carriers have further to travel to reach the surface of the wafer due to the deeper penetration of the long wavelength light. However, as the minority carrier lifetime or diffusion length in the bulk of the wafer increases, the number of minority carriers that successfully migrate near the wafer surface and undergo photoluminescence increases. Thus, the ratio or difference between the captured photoluminescence for two illumination instances of different wavelength is indicative of the bulk carrier lifetime or the bulk carrier diffusion length.

In yet another aspect, inspection system 100 supplies an illumination light to a wafer over a focused illumination spot and images the photoluminescence emitted from the surface of the wafer over a larger area around the illumination spot. Inspection system 100 determines a spatial distribution of the luminous intensity of the photoluminescence. Based on the spatial distribution of the luminescence intensity of the photoluminescence, inspection system 100 estimates a value of the minority carrier lifetime or diffusion length in the bulk of the wafer.

Figure 23:
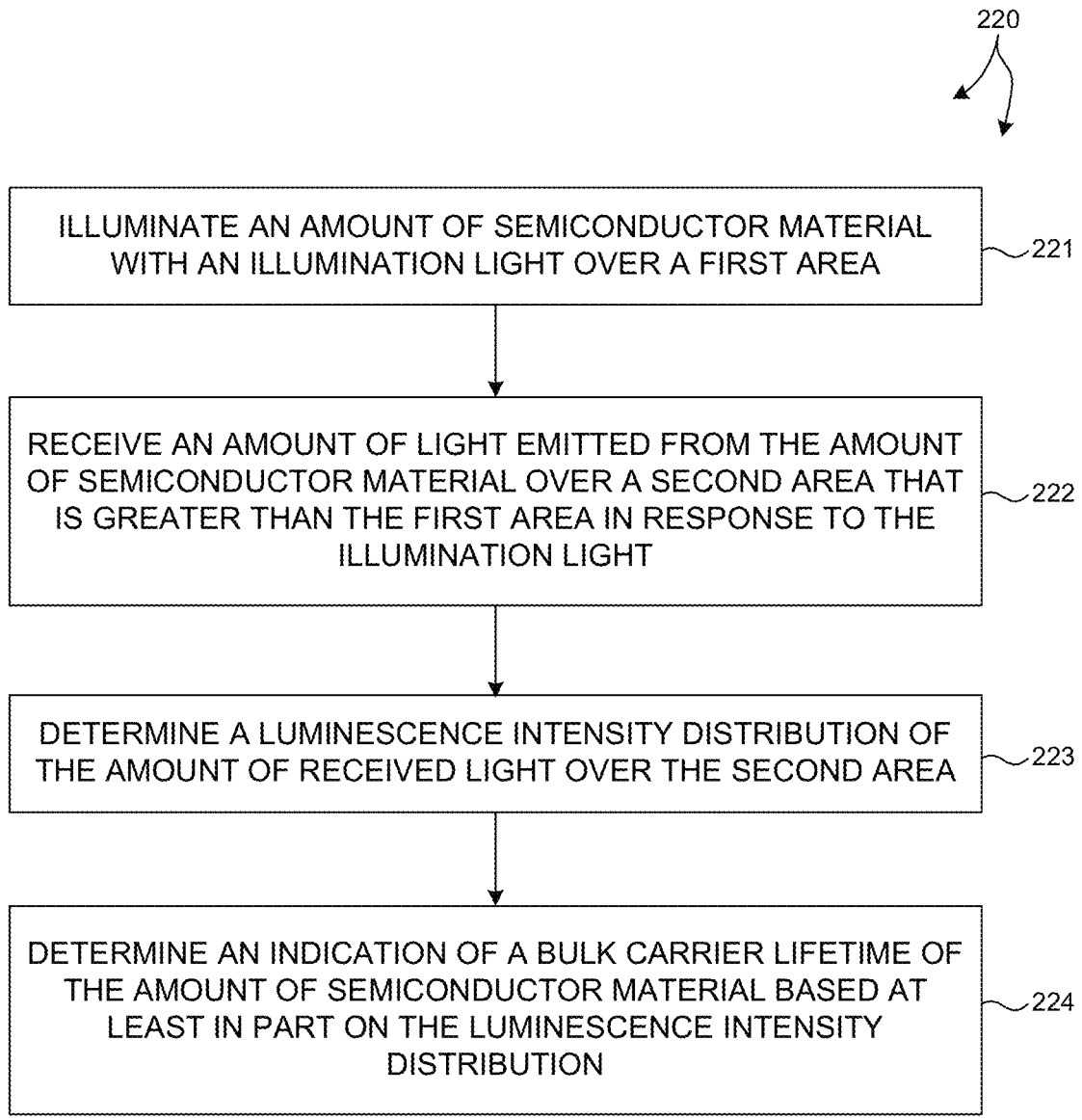
FIG. 23 is a flowchart illustrative of a method 220 of measuring the photoluminescence of an incoming wafer and determining an indication of the minority carrier lifetime or diffusion length in the bulk of the wafer.

FIG. 23 is a flowchart illustrative of a method 220 of measuring the photoluminescence of an incoming wafer in an area around a relatively small illumination spot and determining an indication of the minority carrier lifetime or diffusion length in the bulk of the wafer based on the measured photoluminescence.

Figure 9:
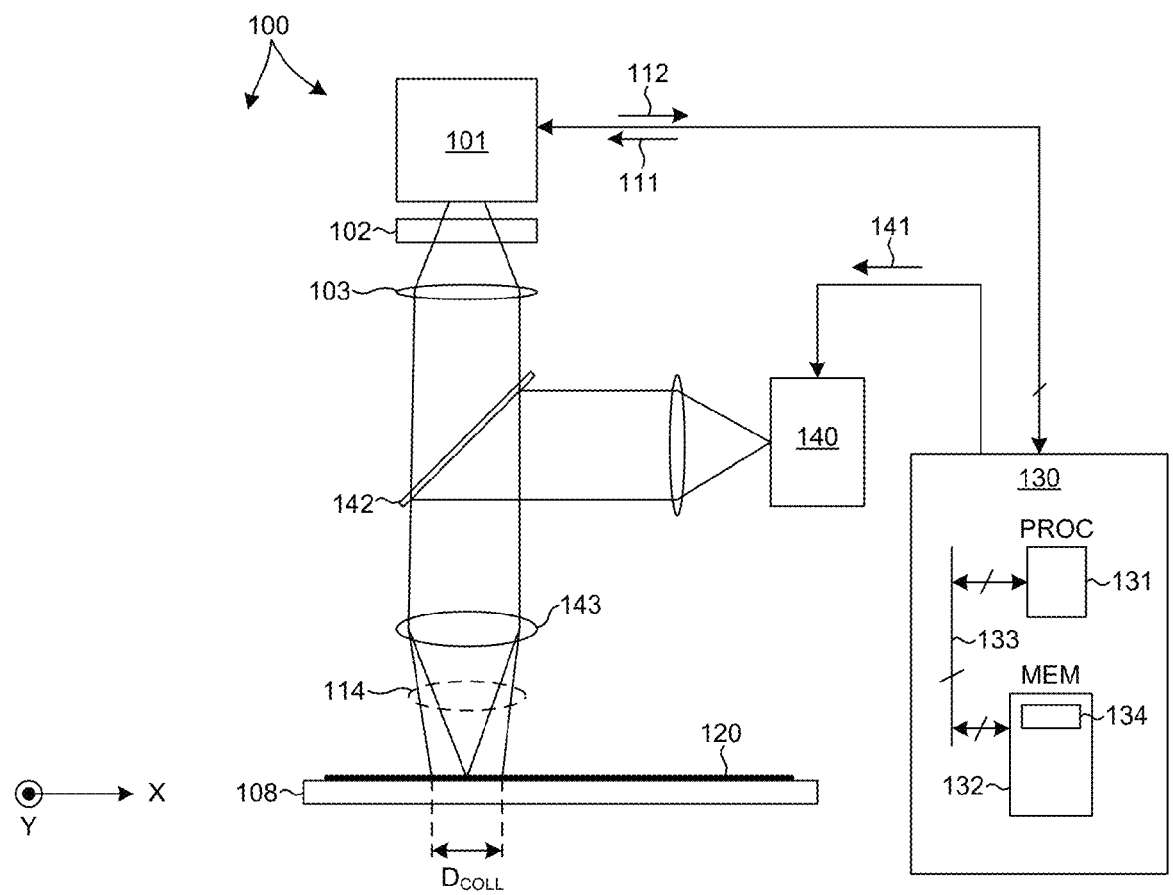
FIG. 9 is a simplified diagram illustrative of another embodiment of an inspection system 100 that may be used to perform the inspection method 220 described herein.

By way of non-limiting example, method 220 will be discussed with reference to the embodiment of inspection system 100 depicted in FIG. 9.

In block 221, inspection system 100 illuminates an amount of semiconductor material with an illumination light over a relatively small area. As illustrated in FIG. 9, an illumination source 140 is configured to generate illumination light directed to the surface of wafer 120. In some embodiments, illumination source 140 is a high power laser capable of delivering light with an intensity of at least 1 milliwatt/mm$^2$ over illumination spot 144 (see FIG. 10) on wafer 120. In some embodiments illumination source 140 is a high power laser capable of delivering light with an intensity of at least 1,000 milliwatts/mm$^2$ over the illumination spot 144 on wafer 120. Such light intensity is useful to saturate the surface of wafer 120 and reduce the likelihood of recombination at the surface of wafer 120 near illumination spot 144. As illustrated in FIG. 9, light is directed to the surface of wafer 120 by a dichroic beamsplitter 142. In one example, controller 130 communicates a command signal 141 to illumination source 140 to illuminate the surface of wafer 120 for a period of time specified by controller 130.

Figure 10:
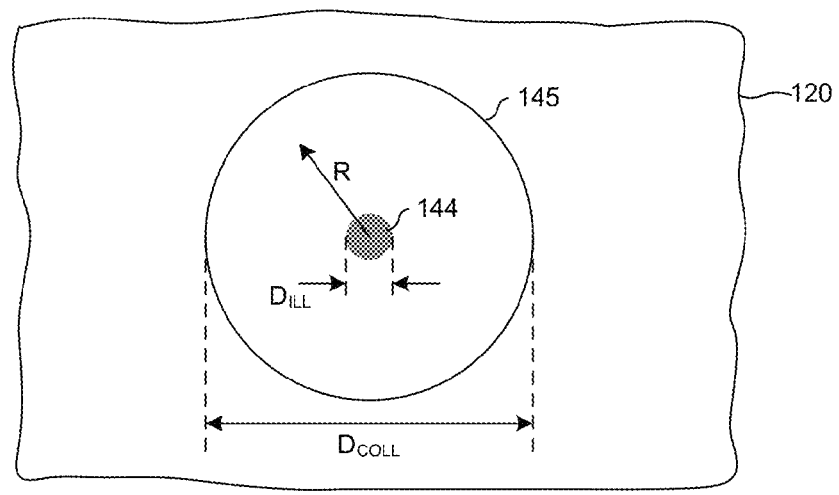
FIG. 10 is a simplified diagram illustrative of an illumination area and an imaging area in accordance with method 220 as described herein.

In block 222, inspection system 100 receives an amount of luminescence emitted from the semiconductor material over a larger area of the wafer surface in response to the illumination light. As illustrated in FIG. 10, light capture device 101 is configured to collect luminescence 114 emitted from the surface of wafer 120 over a collection area 145. Collection area 145 is significantly larger than the illumination spot area 144. In one example, collection area 145 is at least ten times the illumination spot area 144. In one example, controller 130 transmits a command signal 111 to light capture device 101 to trigger the collection of light in synchronization with the light supplied by illumination source 140. Light capture device 101 transmits data signals 112 indicative of the luminescence intensity of the photoluminescence emitted from the surface of wafer 120 as detected by light capture device 101 in response to the illumination light. Controller 130 records the image in memory 132.

Figure 11:
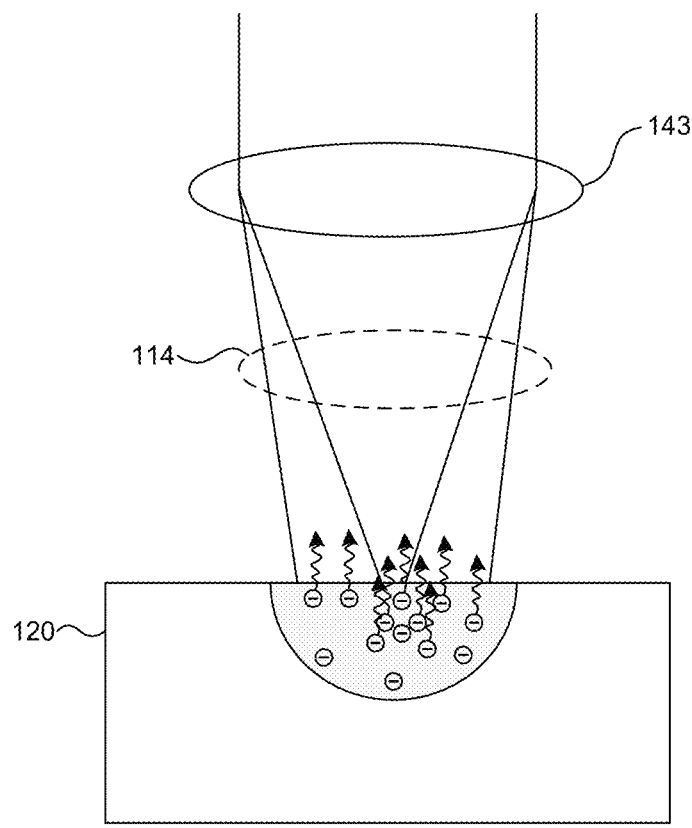
FIG. 11 is a simplified diagram illustrative of electron-hole generation, minority carrier diffusion, and electron-hole recombination in silicon in accordance with method 220 as described herein.
Figure 12:
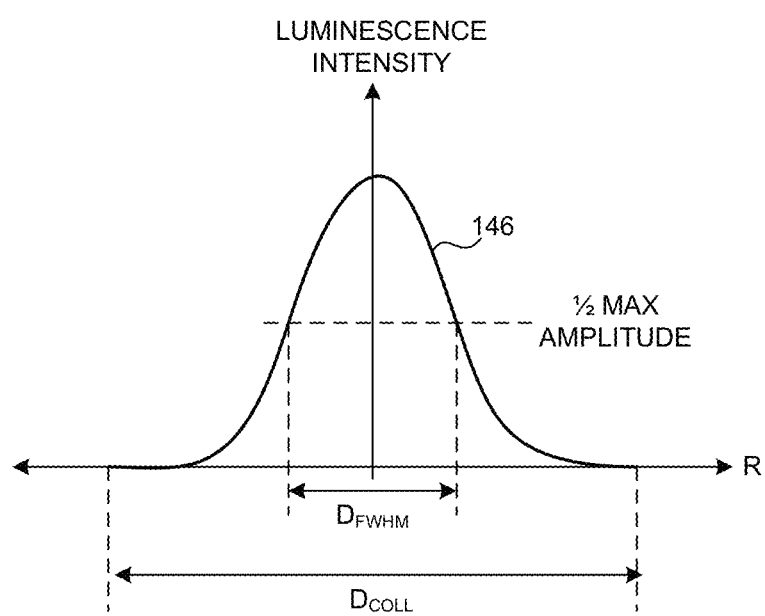
FIG. 12 is a simplified diagram illustrative of an exemplary spatial distribution of luminescence intensity during inspection over a collection area in accordance with method 220 as described herein.

In block 223, inspection system 100 determines a luminescence intensity distribution of the amount of light received over the collection area. As illustrated in FIG. 12, a luminescence intensity distribution 146 centered on the illumination spot 144 is imaged by inspection system 100. As illustrated in FIG. 11, illumination light supplied to wafer 120 over illumination spot 144 generates electron-hole pairs in wafer 120. As discussed hereinbefore, the spatial density of generated electron-hole pairs decreases with distance from the illumination spot 144. After electron-hole generation, the resulting minority carriers begin to diffuse within wafer 120. Minority carriers diffuse from locations of higher concentration of carriers to lower concentration. Some minority carriers migrate into the wafer thickness and recombine in the bulk of wafer 120. Other carriers migrate from the bulk of the wafer 120 toward the surface of the wafer and recombine near the surface where their photoluminescence is captured by light capturing device 101. As the minority carrier lifetime or diffusion length in the bulk of the wafer increases, the average distance of migration of the minority carriers from illumination spot 144 before recombination increases.

In block 224, inspection system 100 determines an indication of the bulk carrier lifetime or the bulk carrier diffusion length based on the luminescence intensity distribution. In one example illustrated in FIG. 12, controller 130 calculates the full width of the distribution 146 at half maximum amplitude, $D_{FWHM}$. $D_{FWHM}$ is the indication of the bulk carrier lifetime or the bulk carrier diffusion length in the wafer 120 at the location under inspection. In other examples, other metrics characterizing the spread of the distribution 146 may be used as indicators of the bulk carrier lifetime or the bulk carrier diffusion length. The width of distribution 146 indicates the distance of migration of the minority carriers from illumination spot 144 before recombination, and thus is indicative of the minority carrier lifetime or diffusion length in the bulk of the wafer.

Figure 13:
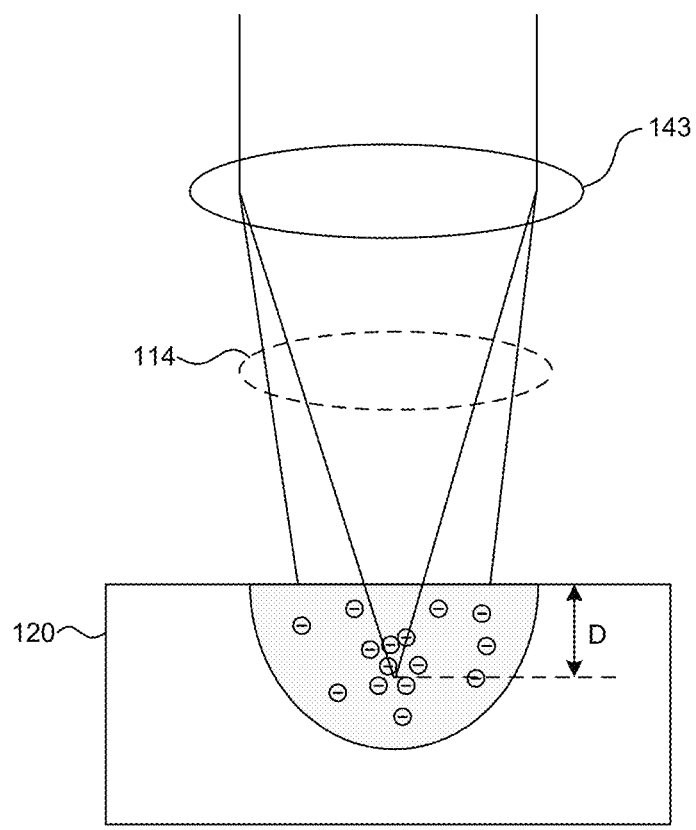
FIG. 13 is a simplified diagram illustrative of electron-hole generation in one example of method 220.

As depicted in FIG. 11, the illumination light is focused on the surface of wafer 120 at high intensity to minimize the effects of surface recombination of as-cut wafers. However, in another embodiment illustrated in FIG. 13, inspection system 100 is configured to focus illumination light at a location within the volume of wafer 120 at a depth, D. By focusing the illumination light within the volume of wafer 120, electron-hole generation is centered at a location below the wafer surface, thus minimizing the effects of surface recombination. However, as illustrated in FIGS. 5 and 6, to achieve a significant penetration depth (e.g., more than 20 micrometers), light with relatively long wavelength must be employed (e.g., greater than 700 nanometers).

In some examples, the estimate of the minority carrier lifetime or diffusion length in the bulk of the wafer from the distribution of the luminescence intensity from an illumination spot can be used to calibrate the indicators of the minority carrier lifetime or diffusion length in the bulk of the wafer determined by other methods described herein. For example, the ratio of photoluminescence intensity for two illumination instances each with a different peak wavelength provides an indication of the minority carrier lifetime or diffusion length in the bulk of the wafer relative to similar ratios taken over different areas of a wafer surface. These indications can be scaled by the estimated value of the minority carrier lifetime or diffusion length in the bulk of the wafer based on the distribution of the luminescence intensity from an illumination spot.

In yet another aspect, the surface of the wafer 120 is temporarily passivated for inspection by any of the methods described herein. By passivating the surface of the wafer, surface recombination can be reduced, allowing photons emitted from electron-hole recombination in the bulk of the wafer to be more visible in the light emitted at the wafer surface.

Figure 16:
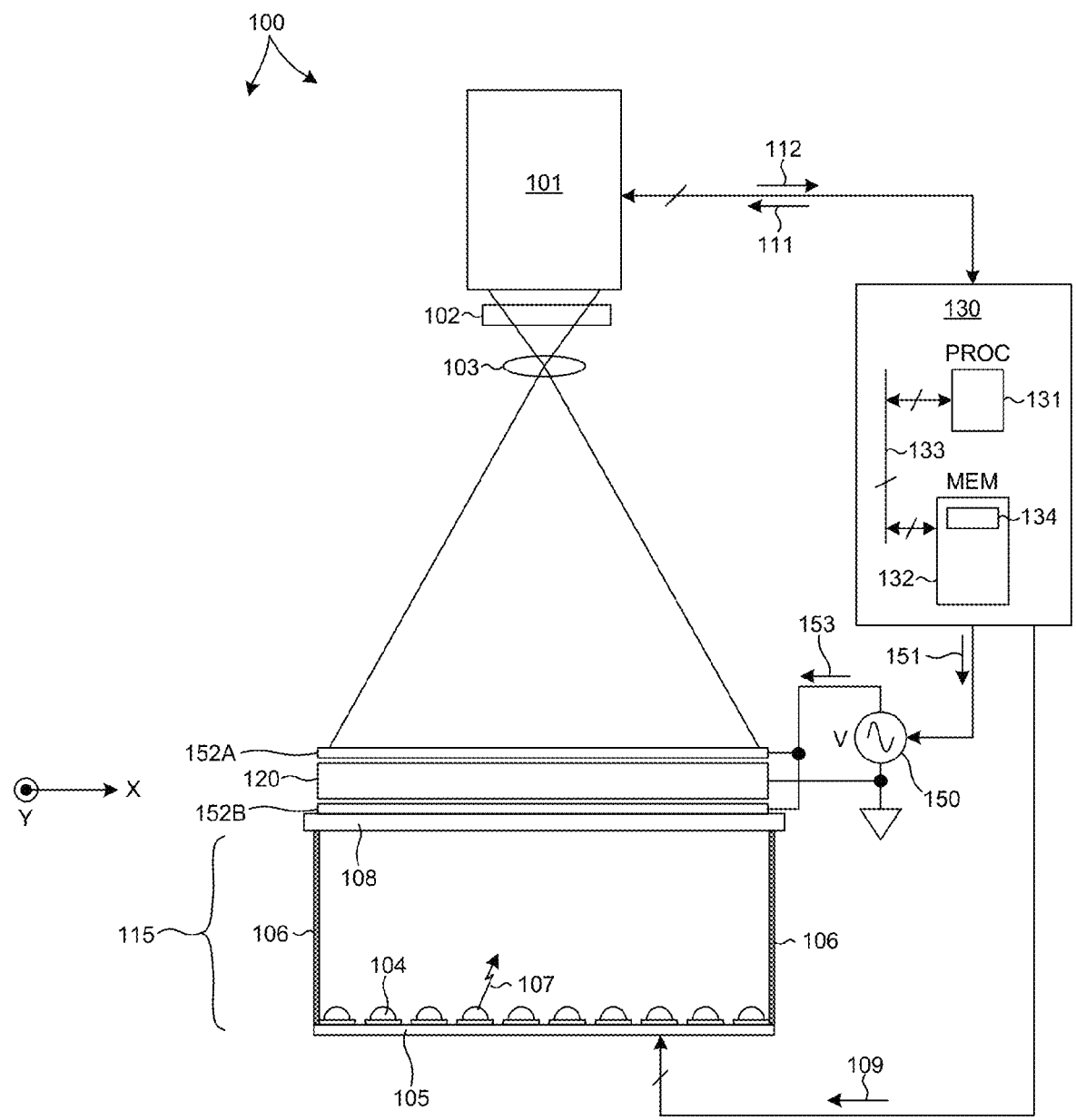
FIG. 16 is a simplified diagram illustrative of another embodiment of an inspection system 100 that may be used to passivate the surface of a wafer during inspection by any of the methods described herein.

In some embodiments, an alternating electrical field is generated slightly above and below the wafer. The alternating electrical field may drive the minority carriers away from the wafer surface and toward the bulk of the wafer. FIG. 16 illustrates inspection system 100 including a transparent, conductive sheet member 152A disposed above the top surface of wafer 120 and transparent, conductive sheet member 152B disposed below the bottom surface of wafer 120. In one example, conductive sheet member 152 is an indium tin oxide coated glass substrate that provides a transparent sheet element that is electrically conductive. An oscillating electrical voltage source 150 is coupled between members 152A and 152B. Oscillating electrical voltage source 150 generates an oscillatory voltage 153 between conductive, transparent sheet elements 152A and 152B. In a preferred embodiment, oscillatory voltage 153 is a sinusoidal voltage signal (e.g., an Alternating Current (AC) voltage signal commonly available in manufacturing environments). In some other embodiments, oscillatory voltage 153 is a square wave signal. Other voltage signal types may be contemplated. Controller 130 transmits a command signal 111 to light capture device 101 to trigger the collection of light in synchronization with a command signal 109 to illuminator 115 to trigger illumination light, and a command signal 151 to oscillating voltage source 150 to trigger the applied electrical field. Light capture device 101 transmits data signals 112 indicative of the luminescence intensity of the photoluminescence emitted from the surface of wafer 120 as detected by light capture device 101 in response to the illumination light. Controller 130 records the image in memory 132. The oscillating electrical field induced in the wafer 120 causes minority carriers to drift alternatively toward and away from the surface of wafer 120 and may reduce the likelihood that a minority carrier recombines at the surface. In this manner, photons emitted from electron-hole recombination in the bulk of the wafer are more visible in the light emitted at the wafer surface.

Figure 17:
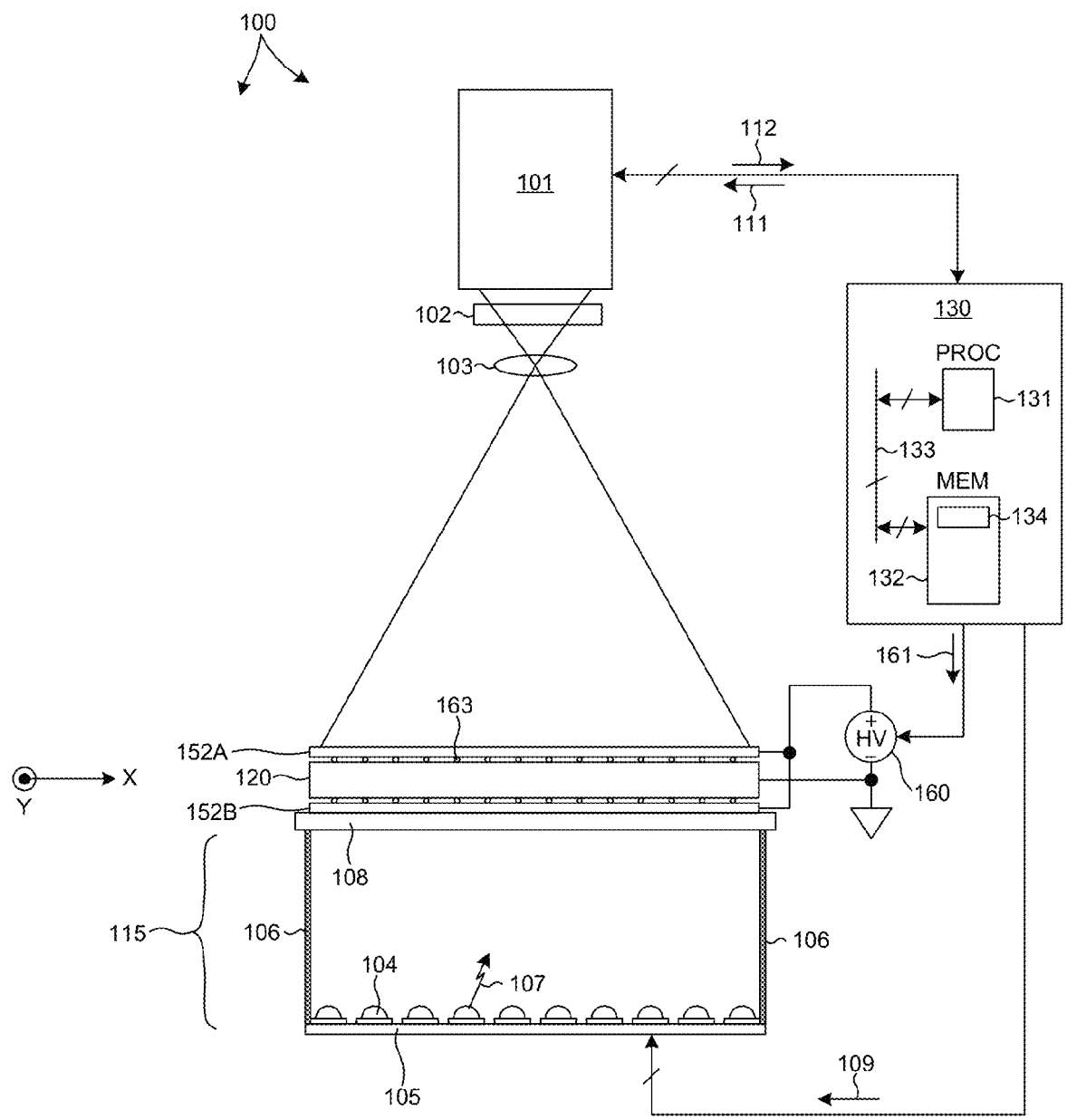
FIG. 17 is a simplified diagram illustrative of yet another embodiment of an inspection system 100 that may be used to passivate the surface of a wafer during inspection by any of the methods described herein.

In some other embodiments, an electrical charge is applied to the surface of the wafer that may drive the minority carriers away from the wafer surface and toward the bulk of the wafer. FIG. 17 illustrates inspection system 100 including a transparent, conductive sheet member 152A disposed above the top surface of wafer 120 and transparent, conductive sheet member 152B disposed below the bottom surface of wafer 120. In one example, conductive sheet member 152 is an indium tin oxide coated glass substrate that provides a transparent sheet element that is electrically conductive. A high voltage power source 160 is coupled between electrical ground and both members 152A and 152B. Wafer 120 is coupled to electrical ground. Voltage source 160 applies a large negative voltage discharge onto both the top and bottom surfaces of the wafer 120. Conductive members 163 (e.g., pins) ensure electrical contact between transparent, conductive sheet members 152 and the surface of the wafer 120. Controller 130 transmits a command signal 111 to light capture device 101 to trigger the collection of light in synchronization with a command signal 109 to illuminator 115 to trigger illumination light, and a command signal 161 to high voltage source 160 to trigger the charging of the wafer surface. Light capture device 101 transmits data signals 112 indicative of the luminescence intensity of the photoluminescence emitted from the surface of wafer 120 as detected by light capture device 101 in response to the illumination light. Controller 130 records the image in memory 132. A negative charge on the surfaces of the wafer may drive minority carriers away from the surface of the wafer toward the middle of wafer 120 and reduce the likelihood that a minority carrier recombines at the surface. In this manner, photons emitted from electron-hole recombination in the bulk of the wafer are more visible in the light emitted at the wafer surface.

Figure 18:
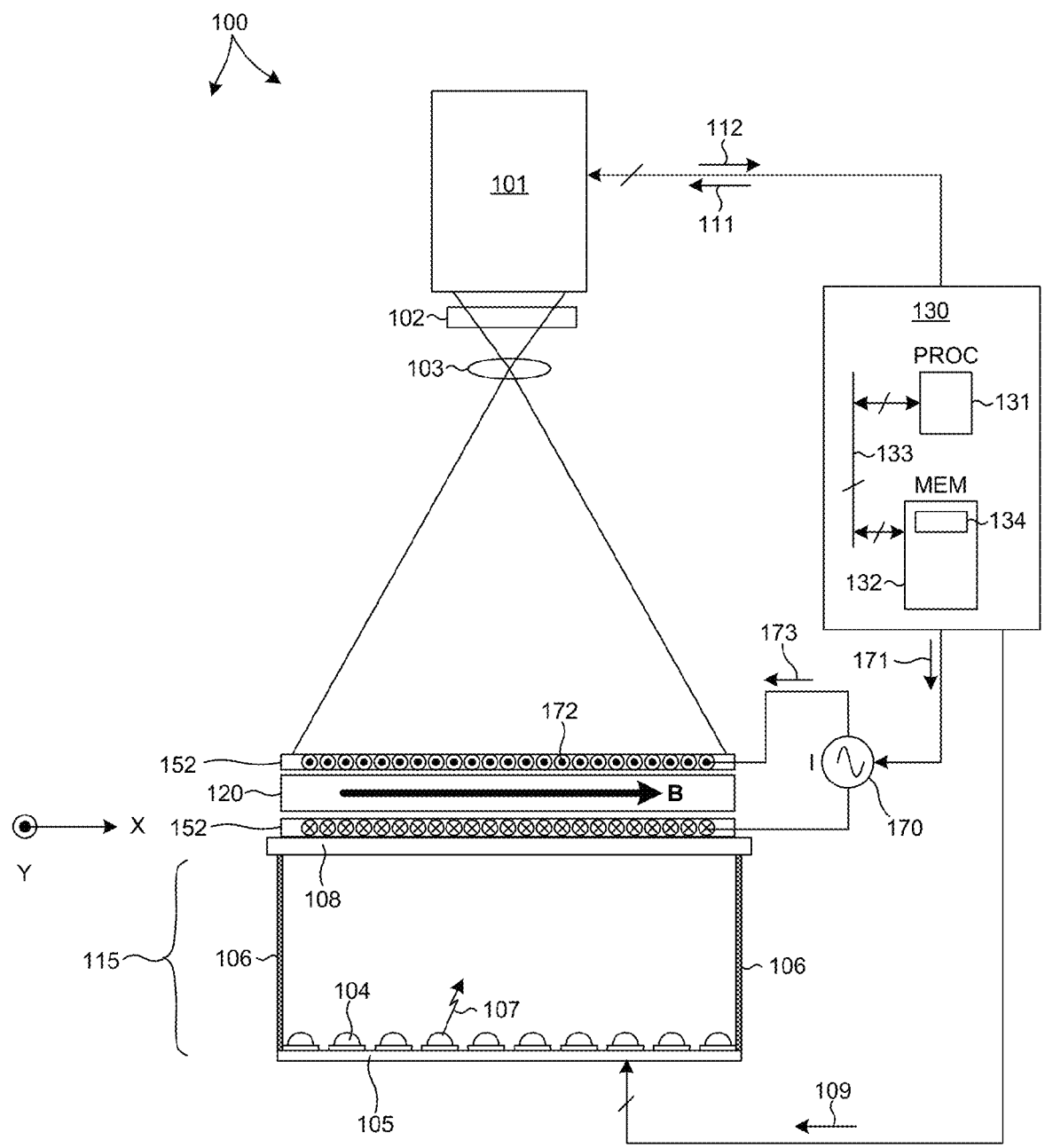
FIG. 18 is a simplified diagram illustrative of yet another embodiment of an inspection system 100 that may be used to passivate the surface of a wafer during inspection by any of the methods described herein.

In some other embodiments, a magnetic field is applied in the plane of the wafer. The applied magnetic field may drive the minority carriers toward the center of the wafer. FIG. 18 illustrates inspection system 100 including a transparent, conductive sheet member 152 disposed above the top surface of wafer 120 and below the bottom surface of wafer 120. In one example, conductive sheet member 152 is a glass substrate coated with traces of indium tin oxide. The traces of indium tin oxide provide a continuous electrical path 172 that wraps around wafer 120. The continuous electrical path 172 forms an electrical coil around wafer 120. An oscillating current source 170 is coupled to the coil shaped electrical path 172. Current source 170 applies an oscillating current through the coil shaped electrical path 172. Controller 130 transmits a command signal 111 to light capture device 101 to trigger the collection of light in synchronization with a command signal 109 to illuminator 115 to trigger illumination light, and a command signal 171 to current source 170 to trigger the supply of oscillating electrical current through path 172. Light capture device 101 transmits data signals 112 indicative of the luminescence intensity of the photoluminescence emitted from the surface of wafer 120 as detected by light capture device 101 in response to the illumination light. Controller 130 records the image in memory 132. The oscillating electrical current flow 173 around wafer 120 induces a magnetic field parallel to the surface of wafer 120. The induced magnetic field may drive minority carriers away from the surface of the wafer toward the middle of wafer 120 and reduce the likelihood that minority carriers recombine at the surface. In this manner, photons emitted from electron-hole recombination in the bulk of the wafer are more visible in the light emitted at the wafer surface.

Figure 19:
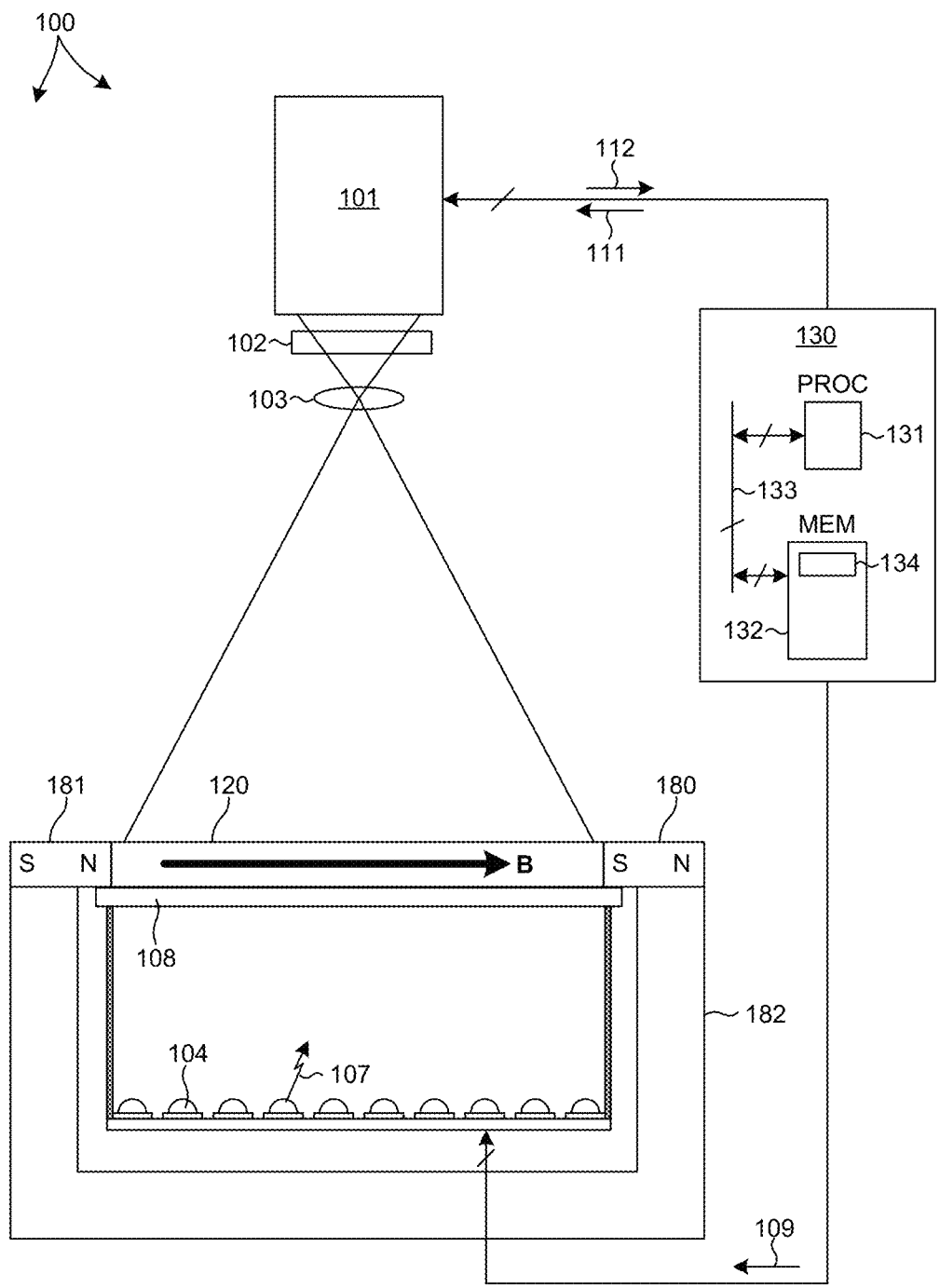
FIG. 19 is a simplified diagram illustrative of yet another embodiment of an inspection system 100 that may be used to passivate the surface of a wafer during inspection by any of the methods described herein.

As illustrated in FIG. 18, a magnetic field is induced parallel to the surface of wafer 120 by an oscillating current flow through a coil enveloping the wafer. In some embodiments, the magnetic field is generated by a permanent magnet. FIG. 19 illustrates a inspection system 100 including permanent magnets 180 and 181 and ferrous material 182 arranged to supply a magnetic field parallel to the surface of wafer 120.

Figure 20:
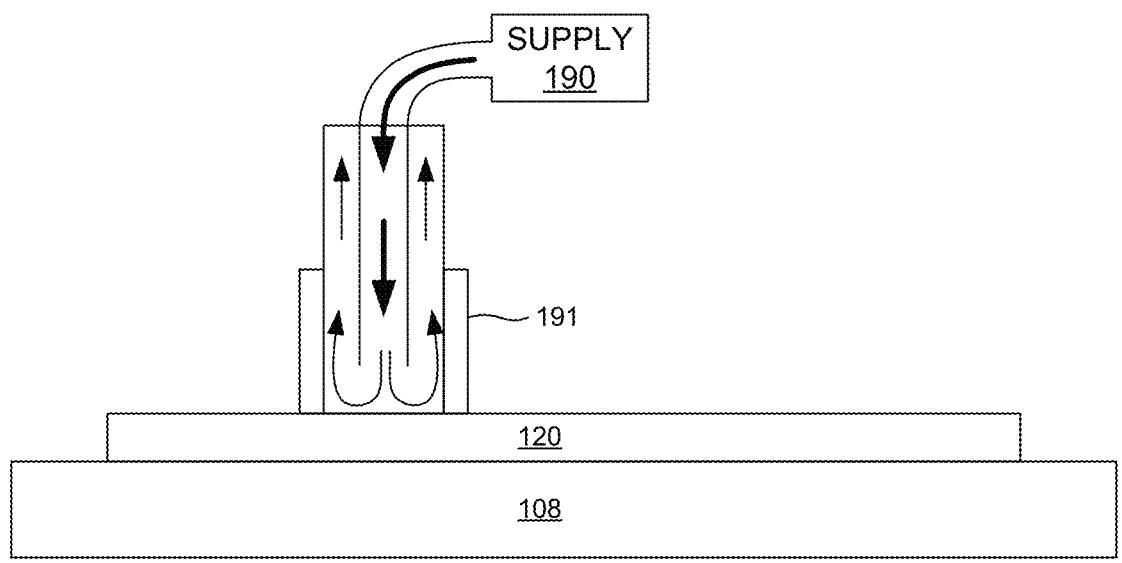
FIG. 20 is a simplified diagram illustrative of an apparatus that may be used to chemically passivate the surface of a wafer for inspection by any of the methods described herein.

In some other embodiments, a surface of wafer 120 is chemically passivated for inspection. FIG. 20 illustrates a micro chemical processor 191 that delivers passivation fluids from a supply reservoir 190 to the surface of the wafer and subsequently evacuates the fluids from the wafer surface after a predetermined period of time. Exemplary passivation chemicals include iodine and solvent mixtures. Chemical reaction between the passivation fluids and the wafer surface may passivate the wafer surface. In this manner, photons emitted from electron-hole recombination in the bulk of the wafer are more visible in the light emitted at the wafer surface.

Although the methods described herein have been described with reference to different embodiments of inspection system 100, an inspection system 100 may implement any combination of the methods of estimating the minority carrier lifetime or diffusion length in the bulk of the wafer described herein without departing from the scope of this description. For example, an inspection system 100 could implement both methods 200 and 210 to determine an indication of a bulk carrier lifetime or diffusion length of wafer 120. Many other combinations of methods and apparatus described herein may be contemplated.

In the depicted embodiments, controller 130 includes a processor 131 and an amount of computer readable memory 132. Processor 131 and memory 132 may communicate over bus 133. Memory 132 includes an amount of memory 134 that stores a program code that, when executed by processor 131, causes processor 131 to determine an indication of a bulk carrier lifetime or diffusion length in accordance with the methods described herein. In addition, memory 132 may include an amount of memory 134 that stores a program code that, when executed by processor 131, causes processor 131 to receive captured images from the luminescence capture device 101, and control operation of the luminescence capture device 101, illumination sources, and other devices in accordance with the methods described herein.

Various embodiments are described herein for an inspection system or tool that may be used for inspecting a specimen. The term "specimen" is used herein to refer to a wafer, a film, or any other sample that may be inspected for defects, features, or other information known in the art.

As used herein, the term "wafer" generally refers to substrates formed of a semiconductor or non-semiconductor material. Examples include, but are not limited to, monocrystalline silicon, quasi-monocrystalline silicon, multicrystalline silicon, gallium arsenide, indium phosphide, and polysilicon. Such substrates may be commonly found and/or processed in semiconductor fabrication facilities. In some cases, a wafer may include only the substrate (i.e., bare wafer). Alternatively, a wafer may include one or more layers of different materials formed upon a substrate. One or more layers formed on a wafer may be "patterned" or "unpatterned." For example, a wafer may include a plurality of dies having repeatable pattern features.

In one or more exemplary embodiments, the functions described may be implemented in hardware, software, firmware, or any combination thereof. If implemented in software, the functions may be stored on or transmitted over as one or more instructions or code on a computer-readable medium. Computer readable media includes both computer storage media and communication media including any medium that facilitates transfer of a computer program from one place to another. A storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

Although certain specific embodiments are described above for instructional purposes, the teachings of this patent document have general applicability and are not limited to the specific embodiments described above. In one example, the methods and apparatus have been described herein with reference to stimulating and detecting photoluminescence. However, the methods and apparatus can be extended to stimulate electroluminescence or a combination of electroluminescence and photoluminescence without departing from the scope of the description provided herein. In another example, inspection system 100 may include more than one light source. The light sources may be configured differently or the same. For example, the light sources may be configured to generate light having different characteristics that can be directed to a wafer at the same or different illumination areas at the same or different angles of incidence at the same or different times. The light sources may be configured according to any of the embodiments described herein. In addition one of the light sources may be configured according to any of the embodiments described herein, and another light source may be any other light source known in the art. In some embodiments, a inspection system 100 may illuminate the wafer 120 over more than one illumination area simultaneously. The multiple illumination areas may spatially overlap. The multiple illumination areas may be spatially distinct. In some embodiments, a inspection system 100 may illuminate the wafer 120 over more than one illumination area at different times. The different illumination areas may temporally overlap (i.e., simultaneously illuminated over some period of time). The different illumination areas may be temporally distinct. In general, the number of illumination areas may be arbitrary, and each illumination area may be of equal or different size, orientation, and angle of incidence. In yet another example, inspection system 100 may be a scanning spot system with one or more illumination areas that scan independently from any motion of wafer 120. In some embodiments an illumination area is made to scan in a repeated pattern along a scan line. The scan line may or may not align with the scan motion of wafer 120. A wafer positioning system may generate motion of wafer 120 in on e direction or by coordinating two translational movements. For example motion wafer positioning system 125 may generate motion along two orthogonal, linear axes (e.g., X-Y motion). Accordingly, various modifications, adaptations, and combinations of various features of the described embodiments can be practiced without departing from the scope of the invention as set forth in the claims.

What is claimed is:

1. A method comprising:
   illuminating an amount of semiconductor material from at least one side with an amount of illumination light;
   receiving a first amount of light emitted from the amount of semiconductor material at the at least one side of the amount of semiconductor material;
   receiving a second amount of light emitted from the amount of semiconductor material at a side opposite the at least one side of the amount of semiconductor material; and
   determining an indication of a bulk carrier lifetime of the amount of semiconductor material based on the first amount of light and the second amount of light.

2. The method of claim 1, wherein the determining of the indication involves determining a difference between the first amount of light and the second amount of light.

3. The method of claim 1, wherein the determining of the indication involves determining a ratio between the first amount of light and the second amount of light.

4. The method of claim 1, wherein the illuminating involves illuminating a first side of the amount of semiconductor material and the receiving the first amount of light involves receiving light emitted from the amount of semiconductor material at the first side in response to the illuminating of the first side, and wherein the illuminating also involves illuminating a side opposite the first side of the amount of semiconductor material and the receiving the second amount of light involves receiving light emitted from the amount of semiconductor material at the first side in response to the illuminating of the side opposite the first side.

5. The method of claim 1, wherein the illuminating involves illuminating a first side of the amount of semiconductor material, the receiving the first amount of light on the first side involves receiving light emitted from the amount of semiconductor material at the first side in response to the illuminating of the first side, and the receiving the second amount of light on the second side involves receiving light emitted from the amount of semiconductor material at a side opposite the first side in response to the illuminating of the first side.

6. The method of claim 1, wherein the amount of illumination light has a peak wavelength between 400 nanometers and 1.1 micrometers.

7. An inspection system, comprising:
   at least one illuminator operable to supply an amount of light to at least one surface of an amount of semiconductor material;
   at least one light capture device operable to receive a first amount of light emitted from the amount of semiconductor material at the at least one surface of the amount of semiconductor material and receive a second amount of light emitted from the amount of semiconductor material at a surface opposite the at least one surface of the amount of semiconductor material; and
   a controller operable to determine an indication of a bulk carrier lifetime of the amount of semiconductor material based on the first amount of light and the second amount of light.

8. The inspection system of claim 7, wherein the at least one illuminator includes a first illuminator operable to supply a first amount of light to a first surface of the amount of semiconductor material and a second illuminator operable to supply a second amount of light to a second surface opposite the first surface.

9. The inspection system of claim 7, wherein the at least one light capture device includes a first light capture device operable to receive a first amount of light emitted from a first surface of the amount of semiconductor material, and a second light capture device operable to receive a second amount of light emitted from a second surface opposite the first surface.

10. The inspection system of claim 7, wherein the indication is a difference between a luminous intensity of the first amount of light and a luminous intensity of the second amount of light.

11. The inspection system of claim 7, wherein the indication is a ratio of a luminous intensity of the first amount of light and a luminous intensity of the second amount of light.

12. A method comprising:
   illuminating an amount of semiconductor material with a first light having a first peak wavelength;
   receiving a first amount of light emitted from the amount of semiconductor material in response to the illuminating of the amount of semiconductor material with the first light;
   illuminating the amount of semiconductor material with a second light, the second light having a second peak wavelength greater than the first peak wavelength;
   receiving a second amount of light emitted from the amount of semiconductor material in response to the illuminating of the amount of semiconductor material with the second light; and
   determining an indication of a bulk carrier lifetime of the amount of semiconductor material based on the first amount of light and the second amount of light.

13. The method of claim 12, wherein the first light has a peak wavelength between 600 nanometers and 1000 nanometers, and wherein the second light has a peak wavelength between 700 nanometers and 1.1 micrometers.

14. The method of claim 13, wherein a difference between the first light and the second light is at least 50 nanometers.

15. The method of claim 12, wherein the determining of the indication involves determining a difference between the first amount of light and the second amount of light.

16. The method of claim 12, wherein the determining of the indication involves determining a ratio between the first amount of light and the second amount of light.

17. A method comprising:
   illuminating an amount of semiconductor material with an illumination light over a first area;
   receiving an amount of light emitted from the amount of semiconductor material over a second area that is greater than the first area in response to the illuminating of the amount of semiconductor material with the illumination light;
   determining a luminescence intensity distribution of the amount of received light over the second area; and determining an indication of a bulk carrier lifetime of the film of semiconductor material based at least in part on the luminescence intensity distribution.

18. The method of claim 17, wherein the illumination light is focused on the surface of the amount of semiconductor material.

19. The method of claim 17, wherein the illumination light is focused at a location within the amount of semiconductor material.

20. The method of claim 17, wherein the intensity of the illumination light is greater than 1 mW/mm$^2$.

21. The method of claim 17, wherein the intensity of the illumination light is greater than 1,000 mW/mm$^2$.

* * * * *